US009434768B2

(12) United States Patent
Cattaneo et al.

(10) Patent No.: US 9,434,768 B2
(45) Date of Patent: Sep. 6, 2016

(54) VIRUSES LACKING EPITHELIAL CELL RECEPTOR ENTRY

(71) Applicant: Mayo Foundation for Medical Education and Research, Rochester, MN (US)

(72) Inventors: Roberto Cattaneo, Rochester, MN (US); Vincent H. J. Leonard, Watertown, MA (US)

(73) Assignee: Mayo Foundation for Medical Education and Research, Rocherster, MN (US)

( * ) Notice: Subject to any disclaimer, the term of this patent is extended or adjusted under 35 U.S.C. 154(b) by 32 days.

(21) Appl. No.: 14/249,821

(22) Filed: Apr. 10, 2014

(65) Prior Publication Data

US 2014/0234943 A1 Aug. 21, 2014

Related U.S. Application Data

(63) Continuation of application No. 12/933,637, filed as application No. PCT/US2009/036950 on Sep. 20, 2010, now Pat. No. 8,709,713.

(60) Provisional application No. 61/038,503, filed on Mar. 21, 2008.

(51) Int. Cl.
*C12P 19/34* (2006.01)
*C07K 14/005* (2006.01)
*A61K 39/165* (2006.01)
(Continued)

(52) U.S. Cl.
CPC ............ *C07K 14/005* (2013.01); *A61K 39/12* (2013.01); *A61K 39/165* (2013.01); *C12N 7/00* (2013.01); *A61K 31/7088* (2013.01); *A61K 31/711* (2013.01); *A61K 31/7105* (2013.01); *A61K 2039/5254* (2013.01); *C12N 15/00* (2013.01); *C12N 15/09* (2013.01); *C12N 2760/18422* (2013.01); *C12N 2760/18434* (2013.01); *C12N 2760/18461* (2013.01)

(58) Field of Classification Search
CPC .................... A61K 39/12; A61K 2039/6031; A61K 39/155; C07K 14/005
See application file for complete search history.

(56) References Cited

U.S. PATENT DOCUMENTS 4,683,195 A 7/1987 Mullis et al.
5,578,448 A 11/1996 Rota et al.
(Continued)

FOREIGN PATENT DOCUMENTS

WO WO 03/093431 11/2003

OTHER PUBLICATIONS

Bowden, et al. Molecular Characterization of Menangle Virus, a Novel Paramyxovirus which Infects Pigs, Fruit Bats, and Humans, Virology, 2001; 283:358-373.*
(Continued)

*Primary Examiner* — Daniel E Kolker
*Assistant Examiner* — Stuart W Snyder
(74) *Attorney, Agent, or Firm* — Fish & Richardson P.C.

(57) ABSTRACT

The document provides nucleic acids, polypeptides, and viruses containing nucleic acids and/or polypeptides. The document also provides methods for using viruses to treat cancer patients. Specifically, the document provides nucleic acid molecules encoding viral hemagglutinin (H) polypeptides, viral H polypeptides, and viruses containing nucleic acids and/or H polypeptides. Such viruses are useful for vaccinations and for treating cancer patients as the viruses are not shed.

12 Claims, 9 Drawing Sheets

| Cell line | Origin | Permissivity $WT_{green}$ | $MVvacNSe_{green}$ |
|---|---|---|---|
| H358 | Human lung | + | + |
| H441 | Human lung | + | + |
| H23 | Human lung | - | + |
| H522 | Human lung | - | + |
| S C aB ER | Human urinary bladder | - | + |
| T24 | Human urinary bladder | - | + |
| HT-1376 | Human urinary bladder | + | + |
| B95a | Marmoset B Lymphocyte | + | + |
| Vero/hSLAM | AGM Kidney | + | + |
| Vero | AGM Kidnet | - | + |

(51) Int. Cl.

| | |
|---|---|
| ***C12N 7/00*** | (2006.01) |
| ***A61K 39/12*** | (2006.01) |
| *A61K 31/711* | (2006.01) |
| *C12N 15/09* | (2006.01) |
| *A61K 31/7088* | (2006.01) |
| *A61K 31/7105* | (2006.01) |
| *C12N 15/00* | (2006.01) |
| *A61K 39/00* | (2006.01) |

(56) References Cited

U.S. PATENT DOCUMENTS 6,416,997 B1 7/2002 Mir Shekari et al.
2005/0042229 A1 2/2005 Yang et al.

OTHER PUBLICATIONS

Patterson, et al. Structural and Functional Studies of the Measles Virus Hemagglutinin: Identification of a Novel Site Required for CD46 Interaction. Virology, 1999; 256: 142-151.*

Air et al., "Evolutionary changes in influenza B are not primarily governed by antibody selection," *Proc. Natl. Acad. Sci.U.S.A.* 1990; 87(10): 3884-3888.

Andre, "Worldwide experience with the Oka-strain live varicella vaccine," *Postgrad Med J.*, 1985, 61(Suppl. 4):113-120.

Cherry, "Measles Virus," In *Textbook of Pediatric Infectious Diseases*, 2004, C.J. Buck, Demmler G., Kaplan S., editor: Elsevier Health Sciences, pp. 2383-2304.

Condack et al., "Measles virus vaccine attenuation: suboptimal infection of lymphatic tissue and tropism alteration," *J. Infect. Dis.*, 2007, 196:541-549.

Crennell et al., "Crystal structure of the multifunctional paramyxovirus hemagglutinin-neuraminidase," *Nat. Struct. Biol.*, 2000, 7:1068-1074.

de Swart et al., "Predominant infection of CD150+ lymphocytes and dendritic cells during measles infection virus ion of macaques," *PLoS Pathogens*, 2007, 3:1771-1781.

Devaux et al., "Attenuation of V- or C-Defective Measles Viruses: Infection Control by the Inflammatory and Interferon Responses of Rhesus Monkey," *J. Virol.*, 2008, 82(11):5359-5367.

Duprex et al., "Observation of measles virus cell-to-cell spread in astrocytoma cells by using a green fluorescent protein-expressing recombinant virus," *J. Virol.*, 1999, 73:9568-9575.

Ehrengruber, et al., "Gene Transfer into Neurons from Hippocampal Slices: Comparison of Recombinant Semliki Forest Virus, Adenovirus, Adeno-Associated Virus, Lentivirus, and Measles Virus," *Mol. Cell. Neurosci.*, 2001; 17: 855-871.

GenBank Accession No. AAD18008, dated Mar. 4, 1999, 1 page.

GenBank Accession No. AAD25093, dated Mar. 27, 2000, 1 page.

GenBank Accession No. AAF85673, dated Jan. 25, 2001, 1 page.

GenBank Accession No. CAA31903.1, dated Apr. 18, 2005, 2 pages.

GenBank Accession No. NC_001498, dated Mar. 9, 2011, 8 pages.

GenBank Accession No. NP_056923, dated Mar. 9, 2011, 2 pages.

Griffin, "Measles virus," In *Fields of Virology*, 2007, Lippincott Williams and Wilkins, pp. 1551-1585.

Hu et al., "Molecular characterization of epitopes on the measles virus hemagglutinin protein," *Virology*, 1993, 192:351-354.

Huber et al., "Measles virus phosphoprotein retains the nucleocapsid protein in the cytoplasm," *Virology*, 1991, 185:299-308.

Karp et al., "An in vitro model of differentiated human airway epithelia. Methods for establishing primary cultures," *Methods Mol. Biol.*, 2002, 188:115-137.

Leonard et al., "Measles virus blind to its epithelial cell receptor remains virulent in rhesus monkeys but cannot cross the airway epithelium and is not shed," *J. Clin. Invest.*, Jul. 2008, 118(7):2448-2458.

Mateo et al., "Structural basis of efficient contagion: measles variations on a theme by parainfluenza viruses," *Curr Opin Virol.*, 5C:16-23, Epub Jan. 31, 2014.

Navarantnarajah, et al. Dynamic Interaction of the Measles Virus Hemagglutinin with Its Receptor Signaling Lymphocytic Activation Molecule (SLAM, CD150). *J. Biol. Chem.* 2008; 283(17) 11763-11771*A.

Navaratnarajah et al., "Dynamic Interaction of the Measles Virus Hemagglutinin with Its Receptor Signaling Lymphocytic Activation Molecule (SLAM, CD150)," *Journal of Biological Chemistry*, Apr. 25, 2008, 283(17):11763-11771.

Nies and Spielberg, "Principles of Therapeutics," In Goodman & Gilman's *The Pharmacological Basis of Therapeutics*, eds. Hardman, et al., McGraw-Hill, NY, 1996, pp. 43-62.

Radecke et al., "Rescue of measles viruses from cloned DNA," *Embo J.*, 1995, 14:5773-5784.

Reyes del Valle et al., "A Vectored Measles Virus Induces Hepatitis B Surface Antigen Antibodies While Protecting Macaques against Measles Virus Challenge," *J. Virol.*, 2007, 81:10597-10605.

Riddell et al., "Review of the temporal and geographical distribution of measles virus genotypes in the prevaccine and postvaccine eras," *Virol. J.*, 2005, 2:87.

Rota et al., "Detection of measles virus RNA in urine specimens from vaccine recipients," *J. Clin. Microbiol.*, 1995, 33:2485-2488.

Santiago et al., "Distinct kinetics for binding of the CD46 and SLAM receptors to overlapping sites in the measles virus hemagglutinin protein," *J. Biol. Chem.*, 2002, 277:32294-32301.

Schaumann et al., "The program FANTOM for energy refinement of polypeptides and proteins using a Newton—Raphson minimizer in torsion angle space," *Biopolymers*, 1990, 29:679-694.

Scheider et al. "Rescue of measles virus using a replication-deficient vaccinia-T7 vector," *J. Virol. Methods*, 1997, 64:57-64.

Sheshberadaran et al., "Characterization of epitopes on the measlesvirus hemagglutinin," *Virology*, 1986, 152:58-65.

Sinn et al., "Measles Virus Preferentially Transduces the Basolateral Surface of Well-Differentiated Human Airway Epithelia," *J. Virol.*, 2002, 76:2403-2409.

Tahara et al., "Multiple Amino Acid Substitutions in Hemagglutinin Are Necessary for Wild-Type Measles Virus to Acquire the Ability to Use Receptor CD46 Efficiently," *J. Virol.*, Mar. 2007, 81(6):2564-2572.

Takeda et al., "Recovery of pathogenic measles virus from cloned cDNA," *J. Virol.*, 2000, 74:6643-6647.

Veskari et al., "Evaluation of Live Attenuated Varicella Vaccine (Oka-RIT Strain) and Combined Varicella and MMR Vaccination in 13-17-Month-Old Children," *Acta paediatr. Scand*,.1991, 80:1051-1057.

von Messling et al., "Receptor (SLAM [CD150]) recognition and the V protein sustain swift lymphocyte-based invasion of mucosal tissue and lymphatic organs by a morbillivirus," *J. Virol.*, 2006, 80:6084-6092.

von Messling et al., "Tropism illuminated: Lymphocyte-based pathways blazed by lethal morbillivirus through the host immune system," *Proc. Natl. Acad. Sci. USA*, 2004, 101:14216-14221.

Vongpunsawad et al., "Selectively Receptor-Blind Measles Viruses: Identification of Residues Necessary for SLAM- or CD46-Induced Fusion and Their Localization on a New Hemagglutinin Structural Model," *J. Virol.*, 2004, 78(1):302-313.

Zabner et al., "Adenovirus-mediated gene transfer to ciliated airway epithelia requires prolonged incubation time ," *J. Virol.*, 1996, 70:6994-7003.

Zhang et al., "Structure of measles virus hemagglutinin bound to its epithelial receptor nectin-4," *Nat Struct Mol Biol.*, 20(1):67-72, Epub Dec. 2, 2012.

Zhu et al., "Experimental Measles. II. Infection and Immunity in the Rhesus Macaque," *Virology*, 233(1):85-92, Jun. 23, 1997.

International Preliminary Report on Patentability for PCT/US2009/036950, issued Sep. 21, 2010,5 pages.

International Search Report and Written Opinion for PCT/US2009/036950, mailed Nov. 2, 2009, 11 pages.

* cited by examiner

| Cell line | Origin | Permissivity $WT_{green}$ | Permissivity $MVvacNSe_{green}$ |
|---|---|---|---|
| H358 | Human lung | + | + |
| H441 | Human lung | + | + |
| H23 | Human lung | - | + |
| H522 | Human lung | - | + |
| S C aB ER | Human urinary bladder | - | + |
| T24 | Human urinary bladder | - | + |
| HT-1376 | Human urinary bladder | + | + |
| B95a | Marmoset B Lymphocyte | + | + |
| Vero/hSLAM | AGM Kidney | + | + |
| Vero | AGM Kidnet | - | + |

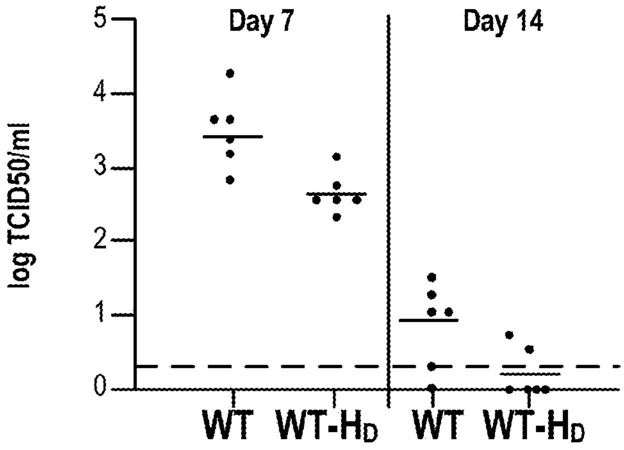
FIG. 4A
| Clinical Signs | WT | WT-HD |
|---|---|---|
| Rash | Yes (2/6) | Yes (4/6) |
| Anorexia | Yes (3/6) | Yes (2/6) |
| Viremia | Yes (6/6) | Yes (6/6) |
| Virus in airways | Yes | No (0/6) |
| Virus in urine | ND | No (0/6) |
FIG. 4B
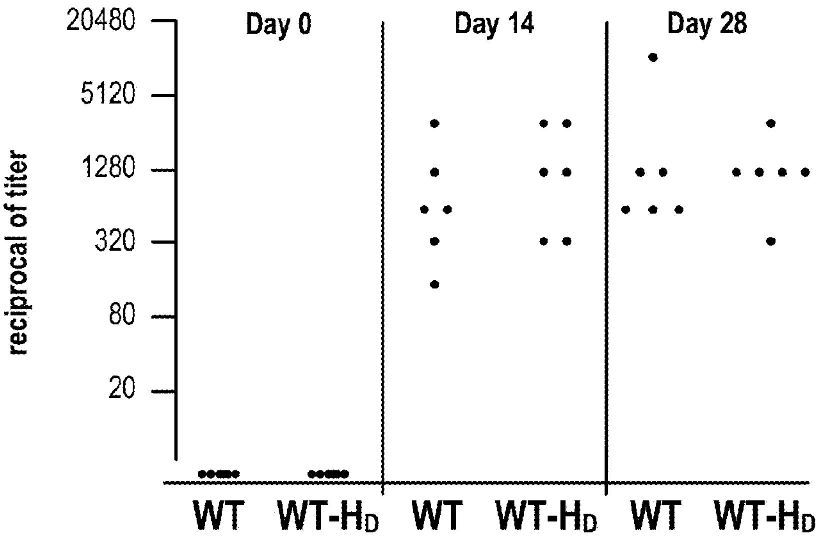
FIG. 4C

SEQUENCE LISTING

```
<160> NUMBER OF SEQ ID NOS: 9

<210> SEQ ID NO 1
<211> LENGTH: 617
<212> TYPE: PRT
<213> ORGANISM: Measles virus

<400> SEQUENCE: 1

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140
```

-continued

```
Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Ala Arg Ala
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Gly Lys Pro Asn Leu Ser
225                 230                 235                 240

Ser Lys Gly Ser Glu Leu Ser Gln Leu Ser Met His Arg Val Phe Glu
                245                 250                 255

Val Gly Val Ile Arg Asn Pro Gly Leu Gly Ala Pro Val Phe His Met
            260                 265                 270

Thr Asn Tyr Phe Glu Gln Pro Val Ser Asn Asp Phe Ser Asn Cys Met
        275                 280                 285

Val Ala Leu Gly Glu Leu Lys Phe Ala Ala Leu Cys His Arg Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Arg Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Asn Gln Ala Leu Cys Glu Asn Pro Glu Trp Ala
385                 390                 395                 400

Pro Leu Lys Asp Asn Arg Ile Pro Ser Tyr Gly Val Leu Ser Val Asn
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Thr Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Asn Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Lys Lys
```

```
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Arg Arg
    610                 615


<210> SEQ ID NO 2
<211> LENGTH: 604
<212> TYPE: PRT
<213> ORGANISM: Canine distemper virus

<400> SEQUENCE: 2

Met Leu Ser Tyr Gln Asp Lys Val Gly Ala Phe Tyr Lys Asp Asn Ala
 1               5                  10                  15

Arg Ala Asn Ser Thr Lys Leu Ser Leu Val Thr Glu Glu His Gly Gly
            20                  25                  30

Arg Arg Pro Pro Tyr Leu Leu Phe Val Leu Leu Ile Leu Leu Val Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Ser Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Ile Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240

Arg Glu Phe Asp Thr Gln Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320
```

-continued

```
Gly Ile Phe Trp Ala Thr Pro Met Asp His Ile Glu Glu Val Ile Pro
                325                 330                 335

Val Ala His Pro Ser Met Glu Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Gln Lys Gly Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asn Gly Thr Ile Val Gly Leu Ile Asn
    450                 455                 460

Lys Ala Gly Arg Gly Asp Gln Phe Thr Val Leu Pro His Val Leu Thr
465                 470                 475                 480

Phe Ala Pro Trp Glu Ser Ser Gly Asn Cys Tyr Leu Pro Ile Gln Thr
                485                 490                 495

Ser Gln Ile Ile Asp Arg Asp Val Leu Ile Glu Ser Asn Ile Val Val
            500                 505                 510

Leu Pro Thr Gln Ser Phe Arg Tyr Val Ile Ala Thr Tyr Asp Ile Ser
        515                 520                 525

Arg Ser Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600


<210> SEQ ID NO 3
<211> LENGTH: 643
<212> TYPE: PRT
<213> ORGANISM: Rinderpest virus

<400> SEQUENCE: 3

Met Ser Ser Pro Arg Asp Arg Val Asn Ala Phe Tyr Lys Asp Asn Leu
 1               5                  10                  15

Gln Phe Lys Asn Thr Arg Val Val Leu Asn Lys Glu Gln Leu Leu Ile
            20                  25                  30

Glu Arg Pro Tyr Met Leu Leu Ala Val Leu Phe Val Met Phe Leu Ser
        35                  40                  45

Leu Val Gly Leu Leu Ala Ile Ala Gly Ile Arg Leu His Arg Ala Ala
    50                  55                  60

Val Asn Thr Ala Glu Ile Asn Ser Gly Leu Thr Thr Ser Ile Asp Ile
65                  70                  75                  80

Thr Lys Ser Ile Glu Tyr Gln Val Lys Asp Val Leu Thr Pro Leu Phe
                85                  90                  95
```

-continued

```
Lys Ile Ile Gly Asp Glu Val Gly Leu Arg Thr Pro Gln Arg Phe Thr
            100                 105                 110

Asp Leu Thr Lys Phe Ile Ser Asp Lys Ile Lys Phe Leu Asn Pro Asp
        115                 120                 125

Lys Glu Tyr Asp Phe Arg Asp Ile Asn Trp Cys Ile Ser Pro Pro Glu
    130                 135                 140

Arg Ile Lys Ile Asn Tyr Asp Gln Tyr Cys Ala His Thr Ala Ala Glu
145                 150                 155                 160

Glu Leu Ile Thr Met Leu Val Asn Ser Ser Leu Ala Gly Thr Ser Val
                165                 170                 175

Leu Pro Thr Ser Leu Val Asn Leu Gly Arg Ser Cys Thr Gly Ser Thr
            180                 185                 190

Thr Thr Lys Gly Gln Phe Ser Asn Met Ser Leu Ala Leu Ser Gly Ile
        195                 200                 205

Tyr Ser Gly Arg Gly Tyr Asn Ile Ser Ser Met Ile Thr Ile Thr Glu
    210                 215                 220

Lys Gly Met Tyr Gly Ser Thr Tyr Leu Val Gly Lys His Asn Gln Gly
225                 230                 235                 240

Ala Arg Arg Pro Ser Thr Ala Trp Gln Arg Asp Tyr Arg Val Phe Glu
                245                 250                 255

Val Gly Ile Ile Arg Glu Leu Gly Leu Gly Thr Pro Val Phe His Met
            260                 265                 270

Thr Asn Tyr Leu Glu Leu Pro Arg Gln Pro Glu Leu Glu Ile Cys Met
        275                 280                 285

Leu Ala Leu Gly Glu Phe Lys Leu Ala Ala Leu Cys Leu Ala Asp Asn
    290                 295                 300

Ser Val Ala Leu His Tyr Gly Gly Leu Arg Asp Asp His Lys Ile Arg
305                 310                 315                 320

Phe Val Lys Leu Gly Val Trp Pro Ser Pro Ala Asp Ser Asp Thr Leu
                325                 330                 335

Ala Thr Leu Ser Ala Val Asp Pro Thr Leu Asp Gly Leu Tyr Ile Thr
            340                 345                 350

Thr His Arg Gly Ile Ile Ala Ala Gly Lys Ala Val Trp Val Val Pro
        355                 360                 365

Val Thr Arg Thr Asp Asp Gln Arg Lys Met Gly Gln Cys Arg Arg Glu
    370                 375                 380

Ala Cys Arg Glu Lys Pro Pro Pro Phe Cys Asn Ser Thr Asp Trp Glu
385                 390                 395                 400

Pro Leu Glu Ala Gly Arg Ile Pro Ala Tyr Gly Ile Leu Thr Ile Arg
                405                 410                 415

Leu Gly Leu Ala Asp Lys Leu Lys Leu Thr Ile Ile Ser Glu Phe Gly
            420                 425                 430

Pro Leu Ile Thr His Asp Ser Gly Met Asp Leu Tyr Thr Pro Leu Asp
        435                 440                 445

Gly Asn Glu Tyr Trp Leu Thr Ile Pro Pro Leu Gln Asn Ser Ala Leu
    450                 455                 460

Gly Thr Val Asn Thr Leu Val Leu Glu Pro Ser Leu Lys Ile Ser Pro
465                 470                 475                 480

Asn Ile Leu Thr Leu Pro Ile Arg Ser Gly Gly Gly Asp Cys Tyr Thr
                485                 490                 495

Pro Thr Tyr Leu Ser Asp Leu Ala Asp Asp Asp Val Lys Leu Ser Ser
            500                 505                 510
```

```
Asn Leu Val Ile Leu Pro Ser Arg Asn Leu Gln Tyr Val Ser Ala Thr
        515                 520                 525

Tyr Asp Thr Ser Arg Val Glu His Ala Ile Val Tyr Tyr Ile Tyr Ser
    530                 535                 540

Ala Gly Arg Leu Ser Ser Tyr Tyr Tyr Pro Val Lys Leu Pro Ile Lys
545                 550                 555                 560

Gly Asp Pro Val Ser Leu Gln Ile Gly Cys Phe Pro Trp Gly Leu Lys
                565                 570                 575

Leu Trp Cys His His Phe Cys Ser Val Ile Asp Ser Gly Thr Arg Lys
            580                 585                 590

Gln Val Thr His Thr Gly Ala Val Gly Ile Glu Ile Thr Cys Asn Ser
        595                 600                 605

Arg Gln Cys Leu Gly Pro Thr Arg Ser Arg Arg Pro Gly Pro Pro Thr
    610                 615                 620

Ala Val Gly Pro Gly Thr Ala Leu His His Ala Asp Ser Phe Gln Tyr
625                 630                 635                 640

Tyr His Tyr


<210> SEQ ID NO 4
<211> LENGTH: 553
<212> TYPE: PRT
<213> ORGANISM: Measles virus

<400> SEQUENCE: 4

Met Ser Ile Met Gly Leu Lys Val Asn Val Ser Ala Ile Phe Met Ala
 1               5                  10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240
```

-continued

```
Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550
```

<210> SEQ ID NO 5
<211> LENGTH: 617
<212> TYPE: PRT
<213> ORGANISM: Measles virus

<400> SEQUENCE: 5

```
Met Ser Pro Gln Arg Asp Arg Ile Asn Ala Phe Tyr Lys Asp Asn Pro
 1               5                  10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60
```

-continued

```
Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480
```

-continued

```
Tyr Leu Phe Asn Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Glu Gly Met Gly Val Ser Cys Thr Val
        595                 600                 605

Thr Arg Glu Asp Gly Thr Asn Arg Arg
    610                 615


<210> SEQ ID NO 6
<211> LENGTH: 236
<212> TYPE: PRT
<213> ORGANISM: Measles virus

<400> SEQUENCE: 6

Phe Gln Gln Ala Cys Lys Gly Lys Asn Gln Ala Leu Cys Glu Asn Pro
 1               5                  10                  15

Glu Trp Ala Pro Leu Lys Asp Asn Arg Ile Pro Ser Tyr Gly Val Leu
            20                  25                  30

Ser Val Asn Leu Ser Leu Thr Val Glu Leu Lys Ile Lys Ile Ala Ser
        35                  40                  45

Gly Phe Gly Pro Leu Ile Thr His Gly Ser Gly Met Asp Leu Tyr Lys
    50                  55                  60

Thr Asn His Asn Asn Val Tyr Trp Leu Thr Ile Pro Pro Met Lys Asn
65                  70                  75                  80

Leu Ala Leu Gly Val Ile Asn Thr Leu Glu Trp Ile Pro Arg Phe Lys
                85                  90                  95

Val Ser Pro Asn Leu Phe Thr Val Pro Ile Lys Glu Ala Gly Glu Asp
            100                 105                 110

Cys His Ala Pro Thr Tyr Leu Pro Ala Glu Val Asp Gly Asp Val Lys
        115                 120                 125

Leu Ser Ser Asn Leu Val Ile Leu Pro Gly Gln Asp Leu Gln Tyr Val
    130                 135                 140

Leu Ala Thr Tyr Asp Thr Ser Arg Val Glu His Ala Val Val Tyr Tyr
145                 150                 155                 160

Val Tyr Ser Pro Ser Arg Ser Phe Ser Tyr Phe Tyr Pro Phe Arg Leu
                165                 170                 175

Pro Ile Lys Gly Val Pro Ile Glu Leu Gln Val Glu Cys Phe Thr Trp
            180                 185                 190

Asp Lys Lys Leu Trp Cys Arg His Phe Cys Val Leu Ala Asp Ser Glu
        195                 200                 205

Ser Gly Gly His Ile Thr His Ser Gly Met Val Gly Met Gly Val Ser
    210                 215                 220

Cys Thr Val Thr Arg Glu Asp Gly Thr Asn Arg Arg
225                 230                 235
```

-continued

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ccttaattaa atgggtctca aggtgaacgt 30

<210> SEQ ID NO 8
<211> LENGTH: 37
<212> TYPE: DNA
<213> ORGANISM: Artificial Sequence
<220> FEATURE:
<223> OTHER INFORMATION: Primer

<400> SEQUENCE: 8
agctttgttt aaactcagag cgaccttaca taggatt 37

<210> SEQ ID NO 9
<211> LENGTH: 617
<212> TYPE: PRT
<213> ORGANISM: Measles virus

<400> SEQUENCE: 9

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Leu Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
```

-continued

```
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Arg Arg
    610                 615
```

VIRUSES LACKING EPITHELIAL CELL RECEPTOR ENTRY

CROSS-REFERENCE TO RELATED APPLICATIONS

This application is a continuation of U.S. Ser. No. 12/933,637, filed Sep. 20, 2010, which is a National Stage application under 35 U.S.C. 371 of International Application No. PCT/US2009/036950 having an International Filing Date of Mar. 29, 2009, which claims the benefit of U.S. Provisional Application Ser. No. 61/038,503, filed Mar. 21, 2008. The disclosures of the prior applications are incorporated by reference in their entirety.

STATEMENT AS TO FEDERALLY SPONSORED RESEARCH

This invention was made with government support under CA090636, awarded by the National Institutes of Health. The government has certain rights in the invention.

BACKGROUND

1. Technical Field

This document provides methods and materials related to viruses and the treatment of diseases such as cancer.

2. Background Information

Measles virus (MV) is one of the most contagious human pathogens. It is transmitted by aerosols, infecting a new host via the upper respiratory tract. It is currently thought that MV and other members of the Morbillivirus genus of Paramyxoviridae infect the upper respiratory epithelium from the luminal side before spreading in lymphatic cells. See Cherry 2004. Measles Virus. In *Textbook of Pediatric Infectious Diseases*. C. J. Buck, Demmler G, Kaplan S., editor: Elsevier Health Sciences. 2383-2304; Griffin, D. E. 2007. Measles virus. In *Fields of Virology*: Lippincott Williams and Wilkins 1551-1585. It is undisputed that, eventually, MV infection spreads to many organs including the skin, respiratory and the urogenital tracts. However, no direct evidence exists for primary MV replication in respiratory epithelial cells, whereas rapid and massive spread of morbillivirus infection through lymphatic cells expressing the signal lymphocytic activation molecule (SLAM, CD 150) was recently documented. See von Messling et al. (2006) *J. Virol.* 80:6084-6092.

SUMMARY

This document provides nucleic acids, polypeptides, and viruses containing nucleic acids and/or polypeptides. This document also provides methods for using viruses to treat cancer patients. Specifically, the document provides viral hemagglutinin (H) polypeptides, nucleic acid molecules encoding viral H polypeptides, and viruses containing H polypeptides and/or nucleic acids encoding H polypeptides. Such viruses are useful for vaccinations and for treating cancer patients as the viruses are not shed.

In one aspect, this document relates to an isolated polypeptide that includes an H polypeptide amino acid sequence that aligns with the amino acid sequence set forth in SEQ ID NO:1. The H amino acid sequence comprises at least one amino acid selected from the group consisting of (a) an amino acid other than isoleucine at the position aligning with position 427 of the amino acid sequence; (b) an amino acid other than isoleucine at the position aligning with position 456 of the amino acid sequence; (c) an amino acid other than methionine at the position aligning with position 459 of the amino acid sequence; (d) an amino acid other than leucine at the position aligning with position 464 of the amino acid sequence; (e) an amino acid other than proline at the position aligning with position 480 of the amino acid sequence; (f) an amino acid other than threonine at the position aligning with position 484 of the amino acid sequence; (g) an amino acid other than proline at the position aligning with position 497 of the amino acid sequence; (h) an amino acid other than threonine at the position aligning with position 498 of the amino acid sequence; (i) an amino acid other than tyrosine at the position aligning with position 541 of the amino acid sequence; (j) an amino acid other than tyrosine at the position aligning with position 543 of the amino acid sequence; and (k) an amino acid other than phenylalanine at the position aligning with position 571 of the amino acid sequence. For example, the H polypeptide amino acid sequence can include at least two amino acids selected from the above group.

In one embodiment, the H polypeptide amino acid sequence includes an amino acid other than proline at the position aligning with position 497 of the amino acid sequence and an amino acid other than tyrosine at the position aligning with position 543 of the amino acid sequence. For example, the H polypeptide amino acid sequence can include a serine at the position aligning with position 497 of the amino acid sequence. The H polypeptide amino acid sequence can include an alanine at the position aligning with position 543 of the amino acid sequence. The H polypeptide amino acid sequence can include a serine at the position aligning with position 497 of the amino acid sequence and an alanine at the position aligning with position 543 of the amino acid sequence.

In another embodiments, the H polypeptide amino acid sequence can include a serine at the position aligning with position 456 of the amino acid sequence. The H polypeptide amino acid sequence can include a serine at the position aligning with position 459 of the amino acid sequence. The H polypeptide amino acid sequence can include a serine at the position aligning with position 464 of the amino acid sequence. The H polypeptide amino acid sequence can include a serine at the position aligning with position 480 of the amino acid sequence. The H polypeptide amino acid sequence can include an alanine at the position aligning with position 484 of the amino acid sequence. The H polypeptide amino acid sequence can include an alanine at the position aligning with position 498 of the amino acid sequence. The H polypeptide amino acid sequence can include an alanine at the position aligning with position 541 of the amino acid sequence. The H polypeptide amino acid sequence can include a serine at the position aligning with position 571 of the amino acid sequence.

In another aspect, the document features an isolated nucleic acid molecule, wherein the nucleic acid molecule encodes a polypeptide that includes an H polypeptide amino acid sequence that aligns with the amino acid sequence set forth in SEQ ID NO:1, wherein the H amino acid sequence includes at least one amino acid selected from the group consisting of (a) an amino acid other than isoleucine at the position aligning with position 427 of the amino acid sequence; (b) an amino acid other than isoleucine at the position aligning with position 456 of the amino acid sequence; (c) an amino acid other than methionine at the position aligning with position 459 of the amino acid sequence; (d) an amino acid other than leucine at the position aligning with position 464 of the amino acid sequence; (e) an amino acid other than proline at the position aligning with position 480 of the amino acid sequence; (f) an amino acid other than threonine at the position aligning with position 484 of the amino acid sequence; (g) an amino acid other than proline at the position aligning with position 497 of the amino acid sequence; (h) an amino acid other than threonine at the position aligning with position 498 of the amino acid sequence; (i) an amino acid other than tyrosine at the position aligning with position 541 of the amino acid sequence; (j) an amino acid other than tyrosine at the position aligning with position 543 of the amino acid sequence; and (k) an amino acid other than phenylalanine at the position aligning with position 571 of the amino acid sequence. The nucleic acid molecule further can encode an F polypeptide.

For example, the H polypeptide amino acid sequence can include an amino acid other than proline at the position aligning with position 497 of the amino acid sequence and an amino acid other than tyrosine at the position aligning with position 543 of the amino acid sequence. The H polypeptide amino acid sequence can include a serine at the position aligning with position 497 of the amino acid sequence. The H polypeptide amino acid sequence can include an alanine at the position aligning with position 543 of the amino acid sequence. The H polypeptide amino acid sequence can include a serine at the position aligning with position 497 of the amino acid sequence and an alanine at the position aligning with position 543 of the amino acid sequence.

In another aspect, the document features vectors, cells, or viruses that include an isolated nucleic acid described herein. The vector can be selected from the group consisting of an adenovirus vector, an adeno-associated virus vector, a herpes virus vector, a retrovirus vector, a lentivirus vector, a parvovirus vector, a Sindbis virus vector, an SV40 vector, and a molecular conjugate vector. The cell can be a cell line or a primary cell. For example, the cell line can be selected from the group consisting of a Vero cell line, a Vero/hSLAM cell line, and a Jurkat cell line. The primary cell can be selected from the group consisting of B or T lymphocytes, dendritic cells, macrophages, and cells from resected primary tumors.

In another aspect, the document features cells and viruses that include a polypeptide described herein. The cell can be a cell line or a primary cell. For example, the cell line can be selected from the group consisting of a Vero cell line, a Vero/hSLAM cell line, and a Jurkat cell line. The primary cell can be selected from the group consisting of B or T lymphocytes, dendritic cells, macrophages, and cells from resected primary tumors. The virus can be selected from the group consisting of a measles virus, a canine distemper virus, and a rinderpest virus. In particular, the virus can be a measles virus (e.g., a vaccine strain).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A is a graph of the $TCID_{50}$/mL in a group of six animals infected with $10^{4.5}$ $TCID_{50}$ of WT-$H_{DOUBLE}$. Data of infections with the parental wild type MV were from Devaux et al. (*J. Virol.* 2008, 82(11):5359-5367) for virus and antibody titers, rash, anorexia and viremia, and from de Swart et al. (2007, *PLoS* Pathogens 3:1771-1781). Blood samples were taken on days 7 or 14 post-infection. Each dot represents one animal; the mean of the group is indicated by a horizontal bar. The dashed line represents the limit of detection of the virus. FIG. 4B is a chart listing the clinical signs and detection of virus in secretions. ND, not determined FIG. 4C is a graph of the neutralizing antibody response. Sera obtained at 0, 14, and 28 days post-inoculation were assayed for MV neutralization and results are presented as reciprocals of the titer. Each dot represents an animal.

Like reference symbols in the various drawings indicate like elements.

DETAILED DESCRIPTION

Figures 1A, 1B:
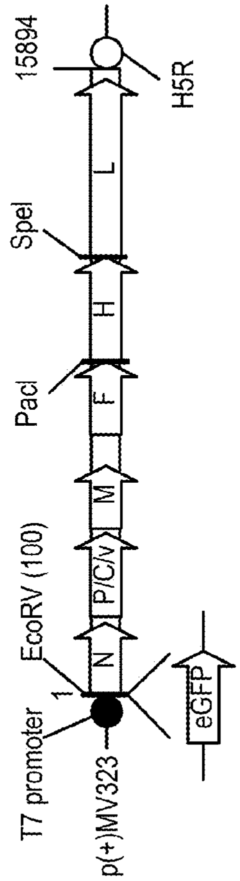
FIG. 1A is a map of the p(+)MV323 plasmid coding for the WT genome and location of the inserted eGFP gene. The coding regions of MV genes are represented by arrowed grey boxes. The T7 promoter, hepatitis delta virus ribozyme (HER), and selected unique restriction sites are indicated. The eGFP transcriptional unit was inserted at an EcoRV restriction site downstream of the N gene transcription start.
FIG. 1B is a chart of MV permissivity of human or primate cells. AGM: African green monkey. (+) infectable; (−) non-infectable.

In general, the document provides nucleic acids, polypeptides, and viruses containing the nucleic acids and/or polypeptides. Specifically, the document provides nucleic acid molecules encoding viral hemagglutinin (H) polypeptides, viral H polypeptides, and viruses containing such nucleic acids and/or such H polypeptides. The viruses described herein can be used for vaccinations and for treating cancer patients as the viruses are not shed.

In particular, the document provides nucleic acid molecules that encode an H polypeptide that (1) is heterologous to any naturally occurring H polypeptide, and (2) confers less epithelial cell receptor (EpR) dependent cell entry to a virus as compared to a naturally occurring H polypeptide. GenBank Accession No. NC_001498 provides the nucleotide sequence encoding the H polypeptide set forth in SEQ ID NO:1. The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acid molecules that are present in a viral genome, including nucleic acids that normally flank one or both sides of the nucleic acid in a viral genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Nucleic acids described herein encode H polypeptides that are heterologous to any naturally occurring viral H polypeptide (i.e., are "modified" H polypeptides). The term "H polypeptide amino acid sequence" as used herein refers to any amino acid sequence that is at least 65 percent (e.g., at least 70, 75, 80, 85, 90, 95, 99, or 100 percent) identical to the sequence set forth in SEQ ID NO:1, SEQ ID NO:2, SEQ ID NO:3, SEQ ID NO:5, or SEQ ID NO:9.

The percent identity between a particular amino acid sequence and the amino acid sequence set forth in SEQ ID NO:1, SEQ ID NO:2, SEQ ID NO:3, SEQ ID NO:5, or SEQ ID NO:9 is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length H polypeptide amino acid sequence followed by multiplying the resulting value by 100. For example, an amino acid sequence that has 500 matches when aligned with the sequence set forth in SEQ ID NO:1 is 81.0 percent identical to the sequence set forth in SEQ ID NO:1 (i.e., 500÷617*100=81.0).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

A mutation in a nucleic acid molecule described herein can be in any portion of the coding sequence that renders the encoded H polypeptide less able than the corresponding, naturally occurring H polypeptide to interact with an epithelial cell receptor. Nucleic acids described herein typically contain nucleotide sequence variants at, for example, positions encoding amino acids involved in EpR binding. Mutations at nucleotides encoding the amino acids at positions 427, 456, 459, 464, 480, 482, 484, 497, 498, 541, 543, or 571 (relative to SEQ ID NO:1, SEQ ID NO:2, SEQ ID NO:3, SEQ ID NO:5, or SEQ ID NO:9) are particularly useful. For example, H polypeptides containing mutations at amino acid positions 427, 541, or 571 have no detectable fusion capacity in H358 cells and low fusion with Vero/hSLAM cells. H polypeptides containing mutations at amino acid positions 456, 459, 464, 480, 484, or 498 have no detectable fusion capacity in H358 cells (epithelial cells) while maintaining more fusion support with Vero/hSLAM cells. H polypeptides containing mutations at amino acid positions 482, 497, or 543 have no detectable fusion capacity in H358 cells while retaining SLAM-dependent fusion support. See, Example 3. Nucleic acids described herein also can include nucleotide sequence variants at positions encoding amino acids that are involved in binding to other molecules, e.g., CD46 and/or SLAM.

Nucleic acids encoding viral H polypeptides can be modified using common molecular cloning techniques (e.g., site-directed mutagenesis) to generate mutations at such positions. Possible mutations include, without limitation, substitutions (e.g., transitions and transversions), deletions, insertions, and combinations of substitutions, deletions, and insertions. Nucleic acid molecules can include a single nucleotide mutation or more than one mutation, or more than one type of mutation. Polymerase chain reaction (PCR) and nucleic acid hybridization techniques can be used to identify nucleic acids encoding H polypeptides having altered amino acid sequences.

Additional nucleic acid sequences can be included in a nucleic acid molecule described herein. Such additional nucleic acid sequences include, without limitation, other viral sequences. For example, a nucleic acid molecule can contain a complete MV genomic sequence that includes, in a 5'-3' direction, the N, P, M, F, H, and L sequences, wherein the naturally occurring H sequence is replaced by a sequence encoding a modified H polypeptide that (1) has an amino acid sequence at least 65% identical to SEQ ID NO:1, SEQ ID NO:2, SEQ ID NO:3, SEQ ID NO:5, or SEQ ID NO:9 and (2) confers less EpR-dependent cell entry to a virus than a corresponding, naturally occurring H polypeptide. A nucleic acid molecule containing such viral nucleic acid sequences can be used to transfect helper cells designed to complement viral replication function (e.g., 293-3-46 cells (Radecke et al. (1995) EMBO 1, 14:5773-5784)) or helper cell lines transiently expressing all the proteins necessary for MV replication (Scheider et al. (1997) *J. Virol. Methods,* 64:57-64) in order to produce infectious virus particles. These cells include primate cells as well as cells of non-primate species expressing a MV receptor, such as CHO cells expressing the SLAM receptor. Alternatively, a nucleic acid molecule can contain sequences that encode a modified H polypeptide and an F polypeptide (including, by way of example and not limitation, an F polypeptide having the amino acid sequence set forth in SEQ ID NO:4). Such a nucleic acid can contain an internal ribosome entry site (IRES) between the coding sequences.

The nucleic acid molecules provided herein also can contain nucleic acid sequences such that the nucleic acid molecules encode replication-competent virus (e.g., replication-competent MV). For example, a nucleic acid molecule described herein can contain viral sequences such that replication-competent viruses expressing modified H polypeptides are produced. As described herein, such a nucleic acid molecule can be an MV cDNA vector containing a nucleic acid sequence encoding a modified H polypeptide.

Alternatively, the nucleic acid molecules provided herein can contain nucleotide sequences such that the nucleic acid molecules encode replication-defective virus (e.g., replication-defective MV). For example, a nucleic acid molecule described herein can contain viral sequences such that replication-defective viruses expressing modified H polypeptides are produced.

Nucleic acids provided herein can encode polypeptides that contain an H polypeptide amino acid sequence coupled to a second amino acid sequence. The second amino acid sequence can be from a polypeptide that is a ligand for a cell surface receptor or that binds to another polypeptide on a cell surface. An amino acid sequence from a single chain antibody or from a growth factor is particularly useful. The second amino acid sequence can be at the amino-terminal end of the amino acid sequence of the H polypeptide extracellular domain, or at the carboxy-terminal end of the H polypeptide amino acid sequence. Location of a second amino acid sequence at the carboxy terminus of the H polypeptide is particular useful.

The document also provides vectors containing nucleic acid that encodes an H polypeptide. Such vectors can be, without limitation, viral vectors, plasmids, phage, and cosmids. For example, vectors can be of viral origin (e.g., paramyxovirus vectors, SV40 vectors, molecular conjugate vectors, or vectors derived from adenovirus, adeno-associated virus, herpes virus, lentivirus, retrovirus, parvovirus, or Sindbis virus) or of non-viral origin (e.g., vectors from bacteria or yeast). A nucleic acid encoding an H polypeptide typically is inserted into a vector such that the H polypeptide is expressed. For example, a nucleic acid provided herein can be inserted into an expression vector. "Expression vectors" can contain one or more expression control sequences (e.g., a sequence that controls and regulates the transcription and/or translation of another sequence). Expression control sequences include, without limitation, promoter sequences, transcriptional enhancer elements, and any other nucleic acid elements required for RNA polymerase binding, initiation, or termination of transcription.

Nucleic acid molecules can be obtained using any method including, without limitation, common molecular cloning and chemical nucleic acid synthesis techniques. For example, PCR can be used to construct nucleic acid molecules that encode modified H polypeptides. PCR refers to a procedure or technique in which target nucleic acid is amplified in a manner similar to that described in U.S. Pat. No. 4,683,195, and subsequent modifications of the procedure described therein.

Nucleic acids provided herein can be incorporated into viruses by standard techniques. For example, recombinant techniques can be used to insert a nucleic acid molecule encoding a modified H polypeptide into an infective viral cDNA. Alternatively, a nucleic acid can be exogenous to a viral particle, e.g., an expression vector contained within a cell such that the polypeptide encoded by the nucleic acid is expressed by the cell and then incorporated into a new viral particle.

This document also provides modified H polypeptides, which are heterologous to naturally occurring H polypeptides. As used here, a "polypeptide" refers to a chain of amino acid residues, regardless of post-translational modification (e.g., phosphorylation or glycosylation). An H polypeptide described herein has an H polypeptide amino acid sequence that is at least 65 percent (e.g., at least 70, 75, 80, 85, 90, 95, 99, or 100 percent) identical to the sequence set forth in SEQ ID NO:1, SEQ ID NO:2, SEQ ID NO:3, SEQ ID NO:5, or SEQ ID NO:9.

Naturally occurring H polypeptides typically have receptor-binding and hemagglutination activities, and functionally cooperate with viral F polypeptides to induce fusion between target cells. Such fusion can be mediated through interactions between H polypeptides and receptors on target cells (e.g., CD46, SLAM, or EpR).

H polypeptides described herein can confer less EpR-dependent cell entry to a virus than would a naturally occurring H polypeptide. For example, when such an H polypeptide is incorporated into a virus, the level of EpR cell entry exhibited by the virus can be less than the level of EpR dependent cell entry exhibited by a wild type virus containing a corresponding, naturally occurring H polypeptide. A measles virus containing an H polypeptide described herein can have less EpR dependent entry into epithelial cells than the amount of EpR-dependent entry of a non-modified MV-Edm into epithelial cells. Cell entry via EpR can be assessed by standard techniques such as those described herein (see Examples 1 and 2). Cells that contain such an H polypeptide along with a naturally occurring F polypeptide (e.g., an F polypeptide having the amino acid sequence set forth in SEQ ID NO:4) can display less EpR fusion than cells containing a naturally occurring H polypeptide that has the amino acid sequence of, for example, SEQ ID NO:1, SEQ ID NO:2, SEQ ID NO:3, SEQ ID NO:5, or SEQ ID NO:9.

H polypeptides described herein that confer reduced EpR-dependent fusion and entry to cells and viruses, respectively, can retain the ability to bind to SLAM and/or CD46. Cells containing such polypeptides therefore can fuse in a CD46- or SLAM-dependent manner, and viruses containing such polypeptides can exhibit CD46- or SLAM-dependent cell entry.

In some embodiments, H polypeptides can have less CD46 binding ability than a corresponding, naturally occurring H polypeptide. Cells that contain such an H polypeptide along with a naturally occurring F polypeptide (e.g., an F polypeptide having the amino acid sequence set forth in SEQ ID NO:4) can display less CD46-dependent fusion than cells containing a naturally occurring H polypeptide that has the amino acid sequence of, for example, SEQ ID NO:1, SEQ ID NO:2, or SEQ ID NO:3. In addition, when such an H polypeptide is incorporated into a virus, the level of CD46-dependent cell entry exhibited by the virus can be less than the level of CD46-dependent cell entry exhibited by a wild type virus containing a corresponding, naturally occurring H polypeptide. For example, a measles virus containing an H polypeptide can have less CD46-dependent entry into $CD46^+$ cells than the amount of CD46-dependent entry of a wild type MV-Edm into $CD46^+$ cells. Cell entry via CD46 receptors can be assessed by standard techniques such as those described in WO 03/093431.

H polypeptides that have reduced CD46 binding and confer reduced CD46-dependent fusion and entry to cells and viruses, respectively, can retain the ability to bind to SLAM. Cells containing such polypeptides therefore can fuse in a SLAM-dependent manner, and viruses containing such polypeptides can exhibit SLAM-dependent cell entry.

In other embodiments, H polypeptides can have less SLAM binding ability than a corresponding, naturally occurring H polypeptide. Cells that contain such an H polypeptide along with a naturally occurring F polypeptide (e.g., an F polypeptide having the amino acid sequence set forth in SEQ ID NO:4) can display less SLAM-dependent fusion than cells containing a naturally occurring H polypeptide that has the amino acid sequence of, for example, SEQ ID NO:1, SEQ ID NO:2, or SEQ ID NO:3. In addition, when such an H polypeptide is incorporated into a virus, the level of SLAM-dependent cell entry exhibited by the virus can be less than the level of SLAM-dependent cell entry exhibited by a wild type virus containing a corresponding, naturally occurring H polypeptide. For example, a measles virus containing an H polypeptide described herein can have less SLAM-dependent entry into SLAM+ cells than the amount of SLAM-dependent entry of a wild type MV-Edm into SLAM+ cells. Cell entry via SLAM receptors can be assessed by standard techniques such as those described in WO 03/093431.

H polypeptides described herein typically contain at least one amino acid substitution relative to the corresponding wild type H polypeptides (e.g., $H_{wtF}$, $H_{Edm}$, or $H_{IC-B}$, the naturally occurring H polypeptides from the wild type F, MV-Edmonston, and Ichinose-B (IC-B) strains, respectively). GenBank Accession No. NP_056923 provides an example of an amino acid sequence of a wild type H polypeptide. Recombinant IC323 is based on the isolate IC-B. An example of an H polypeptide of a vaccine measles strain is provided in GenBank under Accession No. AAF85673 (see SEQ ID NO:9). An example of an H polypeptide of a laboratory measles strain is provided in SEQ ID NO:5. Amino acid substitutions in H polypeptides typically are located at positions involved in the binding of H polypeptides to an EpR Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine.

Non-conservative amino acid substitutions may replace an amino acid of one class with an amino acid of a different class. Non-conservative substitutions can make a substantial change in the charge or hydrophobicity of the gene product. Non-conservative amino acid substitutions also can make a substantial change in the bulk of the residue side chain, e.g., substituting an alanine residue for an isoleucine residue. Examples of non-conservative substitutions include the substitution of a basic amino acid for a non-polar amino acid or a polar amino acid for an acidic amino acid.

Amino acid substitutions that are particularly useful can be found at, for example, one or more positions corresponding to amino acids 427, 456, 459, 464, 480, 482, 484, 497, 498, 541, 543, or 571 of a full-length H polypeptide having the amino acid sequence set forth in SEQ ID NO:1, SEQ ID NO:2, SEQ ID NO:3, SEQ ID NO:5, or SEQ ID NO:9. In some embodiments, an H polypeptide contains two substitutions, e.g., at positions corresponding to amino acids 497 and 543 of a full-length H polypeptide having the amino acid sequence set forth in SEQ ID NO:1, SEQ ID NO:2, or SEQ ID NO:3. Such one or more substitutions can, for example, (1) render the H polypeptide less able than a naturally occurring H polypeptide to bind to EpR, (2) confer less EpR-dependent fusion between cells than would a naturally occurring H polypeptide, or (3) confer less EpR-dependent cell entry to a virus than would a naturally occurring H polypeptide. For example, a serine residue can be substituted for isoleucine at a position aligning with residue 427 or 456 of SEQ ID NO:1, SEQ ID NO:2, or SEQ ID NO:3. A serine residue can be substituted for methionine at a position aligning with residue 459 of SEQ ID NO:1. A serine residue can be substituted for leucine at a position aligning with residue 464 of SEQ ID NO:1, SEQ ID NO:2, or SEQ ID NO:3. A serine residue can be substituted for leucine at a position aligning with residue 482 of SEQ ID NO:1. An alanine residue can be substituted for threonine at a position aligning with residue 484 of SEQ ID NO:1, SEQ ID NO:2, or SEQ ID NO:3. A serine residue can be substituted for proline at a position aligning with residue 497 of SEQ ID NO:1, SEQ ID NO:2, or SEQ ID NO:3. An alanine residue can be substituted for threonine at a position aligning with residue 498 of SEQ ID NO:1 or SEQ ID NO:2. An alanine residue can be substituted for tyrosine at a position aligning with residue 541 or 543 of SEQ ID NO:1, SEQ ID NO:2, or SEQ ID NO:3. A serine residue can be substituted for phenylalanine at a position aligning with residue 571 of SEQ ID NO:1, SEQ ID NO:2, or SEQ ID NO:3. In some embodiments, a serine residue can be substituted for proline at a position aligning with residue 497 and an alanine residue can be substituted for tyrosine at a position aligning with residue 543. Similar substitutions can be made in the amino acid sequences set forth in SEQ ID NO:5 or SEQ ID NO:9.

Other amino acid substitutions can be introduced to an H polypeptide to reduce CD46 and/or SLAM binding in combination with reduced EpR binding. For example, amino acid substitutions that are particularly useful for reducing CD46 binding can be found at, for example, one or more positions corresponding to amino acids 431, 451, 481, and 527 of a full-length H polypeptide having the amino acid sequence set forth in SEQ ID NO:1, SEQ ID NO:2, SEQ ID NO:3, SEQ ID NO:5, or SEQ ID NO:9. Such substitutions (1) render the H polypeptide less able than a naturally occurring H polypeptide to bind to CD46, (2) confer less CD46-dependent fusion between cells than would a naturally occurring H polypeptide, and/or (3) confer less CD46-dependent cell entry to a virus than would a naturally occurring H polypeptide. See WO 03/093431.

Amino acid substitutions that are particularly useful for reducing SLAM binding can be found at, for example, one or more positions corresponding to amino acids 194, 529, 530, 533, and 553 of a full-length H polypeptide having the amino acid sequence set forth in SEQ ID NO:1, SEQ ID NO:2, SEQ ID NO:3, SEQ ID NO:5, or SEQ ID NO:9. Such substitutions (1) render the H polypeptide less able than a naturally occurring H polypeptide to bind to SLAM, (2) confer less SLAM-dependent fusion between cells than would a naturally occurring H polypeptide, and/or (3) confer less SLAM-dependent cell entry to a virus than would a naturally occurring H polypeptide. See WO 03/093431.

H polypeptides provided herein also can contain substitutions from all of the groups defined above. Such H polypeptides typically exhibit less EpR binding, less CD46 binding, and less SLAM binding than a naturally occurring H polypeptide. Cells containing such an H polypeptide can display less EpR-dependent fusion, less CD46-dependent fusion, and less SLAM-dependent fusion than cells expressing a naturally occurring H polypeptide. Furthermore, a virus expressing such an H polypeptide can exhibit less EpR-dependent cell entry, less CD46-dependent cell entry, and less SLAM-dependent entry than a virus expressing a naturally occurring H polypeptide.

An H polypeptide amino acid sequence can be coupled to a second amino acid sequence. Such coupling can occur through, for example, peptide bonding. As used herein, a "second amino acid sequence" is an amino acid sequence that is exogenous to an H polypeptide amino acid sequence. Typically, second amino acid sequences that are particularly useful can bind to cell surface receptors other than SLAM and CD46. Such second amino acid sequences therefore can serve to target an H polypeptide to a particular type of cell (e.g., a tumor cell), depending on the receptor targeted by the second amino acid sequence. Second amino acid sequences from growth factors and single chain antibodies are particularly useful. A second amino acid sequence can be at the amino-terminal end of the amino acid sequence of the H polypeptide extracellular domain, or at the carboxy-terminal end of the H polypeptide amino acid sequence. Localization of a second amino acid sequence at the carboxy terminus of an H polypeptide amino acid sequence is particularly useful.

An H polypeptide that is incorporated into a virus can be encoded by a nucleic acid molecule that is present within the virus. Alternatively, a virus can take up an exogenous H polypeptide that is expressed by, for example, a cell. Amino acid substitutions within viral H polypeptides can result in viruses having, for example, less binding to epithelial cell receptors and less EpR-dependent cell entry than the levels of EpR binding and EpR-dependent cell entry exhibited by viruses containing naturally occurring H polypeptides. Levels of binding to epithelial cell receptors and EpR-dependent cell entry can be measured by techniques such as, for example, those described herein (see Examples 1, 2, and 3).

H polypeptides can be produced using any method. For example, H polypeptides can be obtained by extraction from viruses, isolated cells, tissues and bodily fluids. H polypeptides also can be produced by chemical synthesis. Alternatively, H polypeptides can be produced by standard recombinant technology using heterologous expression vectors encoding H polypeptides. Expression vectors can be introduced into host cells (e.g., by transformation or transfection) for expression of the encoded polypeptide, which then can be purified. Expression systems that can be used for small or large scale production of H polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules, and yeast (e.g., *S. cerevisiae*) transformed with recombinant yeast expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid) containing the nucleic acid molecules. H polypeptides also can be produced using mammalian expression systems, which include cells (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein.

This document provides viruses containing the nucleic acid molecules and/or polypeptides described herein. For example, the document provides recombinant viruses that encode polypeptides (e.g., modified H polypeptides) that are heterologous to a corresponding, naturally occurring H polypeptide.

Viruses containing the nucleic acid molecules described herein are not required to express the encoded polypeptide. For example, a virus (e.g., an Adenovirus, retrovirus, or a herpes simplex virus) can be engineered to contain a nucleic acid that encodes an H polypeptide described herein. In this case, the engineered virus may or may not express the encoded H polypeptide. Viruses containing nucleic acid that encodes an H polypeptide can be used to deliver the nucleic acid to cells, such that the cells express the encoded H polypeptide.

Alternatively, viruses that contain a nucleic acid molecule described herein can express the encoded H polypeptide. For example, an MV containing a nucleic acid molecule that encodes a modified H polypeptide can display the modified H polypeptide on its surface. Such a virus can target cells for viral entry.

Any virus can contain a nucleic acid molecule encoding a modified viral H polypeptide. Viruses can be RNA viruses or DNA viruses. Viruses can be, for example, nonsegmented negative strand RNA viruses belonging to the Mononegavirales group (e.g., MV, human parainfluenzavirus, rabies virus, respiratory syncytial virus, and mumps virus). Viruses also can be influenza viruses, which have a segmented RNA genome of negative polarity and share several structural features with MV. Viruses also can be, without limitation, enveloped viruses such as herpes simplex virus, and retroviruses such as murine leukemia virus and human immunodeficiency virus.

Viruses provided herein can be attenuated. As used herein, the term "attenuated" refers to a virus that is immunologically related to a wild type virus but which is not itself pathogenic. An attenuated MV, for example, does not produce classical measles disease. Attenuated viruses typically are replication-competent, in that they are capable of infecting and replicating in a host cell without additional viral functions supplied by, for example, a helper virus or a plasmid expression construct encoding such additional functions.

Viruses containing a nucleic acid molecule that encodes a modified H polypeptide and that have reduced EpR-dependent cell entry can be replication-competent or replication-defective. In addition, the nucleic acid molecule within the virus can contain any of the nucleic acid sequences described herein. For example, a measles virus can contain a complete MV genome that has a nucleotide sequence encoding a heterologous H polypeptide. Such a virus can display less EpR-dependent cell entry than a wild type virus containing the corresponding, naturally occurring H polypeptide. The level of EpR-dependent cell entry can be assessed by standard techniques such as, for example, those described herein.

Any method can be used to identify viruses containing a nucleic acid molecule described herein. Such methods include, without limitation, PCR and nucleic acid hybridization techniques such as Northern and Southern analysis. In some cases, immunohistochemistry and biochemical techniques can be used to determine if a virus contains a particular nucleic acid molecule by detecting the expression of a polypeptide encoded by that particular nucleic acid molecule.

H polypeptides and/or nucleic acids can be administered to cells in order to induce cell fusion. For example, a nucleic acid molecule (e.g., a viral vector) encoding a modified H polypeptide as well as any other polypeptide (e.g., an F polypeptide) can be administered to a tumor in order to induce fusion between tumor cells, ultimately resulting in cell death.

Viruses that contain nucleic acids and/or polypeptides provided herein also can be administered to cells (e.g., in vivo or in vitro) to induce cell fusion. Incorporation of the encoded H polypeptide into the virus is not required. For example, a virus (e.g., an Adenovirus or a herpes simplex virus) can be engineered to contain a nucleic acid encoding an H polypeptide that is not incorporated into the virus. Such a virus can be administered to a cell population in order to deliver the nucleic acid encoding the H polypeptide into the cells. The infected cells then can express the encoded H polypeptide, leading to cell fusion. Viruses provided herein that contain nucleic acids encoding H polypeptides and contain the H polypeptides also are useful for inducing cell fusion. An MV, for example, that contains a nucleic acid encoding an H polypeptide also can contain the encoded H polypeptide. Such a virus can be used to target particular cells as described herein. The H polypeptide then can be expressed within the targeted cells, inducing the cells to fuse. It is noted that an F polypeptide can be used with the H polypeptides described herein. For example, a single virus can contain nucleic acid that encodes both an H polypeptide and an F polypeptide.

Viruses provided herein can be used for vaccinations. For example, attenuated viruses containing the H polypeptides described herein are particularly useful for vaccinations as such viruses are not shed, i.e., are host escape-incompetent. See, Example 6. Thus, an infectious measles virus with a vaccine strain background can be engineered to include a nucleic acid encoding a modified H polypeptide described herein such that the virus is host escape-incompetent. Such an infectious measles virus can be engineered to have additional vaccine specificities, such as for hepatitis B virus, hepatitis C virus, yellow fever, mumps virus, or West Nile virus, by inserting nucleic acids from the additional virus into the measles virus genome. For example, an infectious measles virus with a vaccine strain background can be engineered to include a nucleic acid encoding a modified H polypeptide described herein and a nucleic acid encoding the hepatitis B surface antigen. See, e.g., Reyes del Valle et al., 2007, *J. Virol.* 81:10597-10605.

In some embodiments, a composition can be formulated that contains an attenuated measles virus described herein. Such a composition can be used as a vaccine. In other embodiments, a composition can be formulated that contains an attenuated measles virus described herein in combination with one or more of the following: an attenuated mumps virus, attenuated rubella virus, and an agent for protection against varicella zoster infection. Trivalent measles, mumps, and rubella vaccines and quadrivalent vaccines providing protection against measles, mumps, rubella, and varicella zoster viruses are well known in the art. An agent for protection against varicella zoster can include a live Varicella Zoster attenuated virus. For example, the Varicella Zoster virus can be the Oka strain as disclosed by Andre

*MED J.* (1985) 61(Suppl. 4):113-120 or Veskari T et al *Acta paediatr. Scand.* 80: 1051-1057, 1991.

In some embodiments, adjuvant is added to a composition containing an attenuated measles virus described herein. Suitable adjuvants can be selected based, for example, on the route of administration and number of administrations. Non-limiting examples of adjuvants include mineral oil adjuvants such as Freund's complete and incomplete adjuvant, and Montanide incomplete seppic adjuvant (ISA, available from Seppic, Inc., Paris, France); oil-in-water emulsion adjuvants such as the Ribi adjuvant system (RAS); TiterMax®, and syntax adjuvant formulation containing muramyl dipeptide; or aluminum salt adjuvants.

Such compositions can be generally useful for inducing immune responses in a subject (e.g., a human) and as prophylactic vaccines. The term "prophylaxis," as used herein, refers to the complete prevention of the symptoms of a disease, a delay in onset of the symptoms of a disease, or a lessening in the severity of subsequently developed disease symptoms.

In some embodiments, a vaccine containing the attenuated measles virus is administered to the subject. In other embodiments, a vaccine containing an attenuated measles virus and an adjuvant is administered to the subject. Generally, the composition to be administered can be suspended in a pharmaceutically-acceptable carrier (e.g., physiological saline) and administered orally, transdermally, intravenously, subcutaneously, intramuscularly, intraocularly, intraperitoneally, intrarectally, intravaginally, intranasally, intragastrically, intratracheally, intrapulmonarily, or any combination thereof. For example, the composition can be administered intranasally and subcutaneously. If desired, booster immunizations may be given once or several times (e.g., 2, 3, or 4 times) at various intervals (e.g., three months apart or three years apart).

Suitable doses of the composition elicit an immune response in the subject but do not cause the subject to develop severe clinical signs of measles. The dose required to elicit an immune response depends on the route of administration, the nature of the composition, the subjects size, weight, surface area, age, and sex, other drugs being administered, and the judgment of the attending physician. Wide variations in the needed dose are to be expected in view of differing efficiencies of various routes of administration. For example, oral administration would be expected to require higher doses than administration by intravenous injection. Variations in these dose levels can be adjusted using standard empirical routines for optimization, as is well understood in the art. Encapsulation of the composition in a suitable delivery vehicle (e.g., polymeric microparticles or implantable devices) may increase the efficiency of delivery, particularly for oral delivery.

To determine if an immune response was induced in the subject, a biological sample from the subject can be examined to determine if it contains detectable amounts of antibodies having specific binding affinity for one or more antigens of the organism the subject was vaccinated against. The biological sample can be blood (e.g., serum) or a mucosal sample (e.g., saliva). Methods for detecting antibodies, including IgG, IgM, and IgA, are known, and can include, for example, enzyme-linked immunosorbent assays (ELISA) or Western blotting. If antibodies are detected, the subject is considered to be seropositive.

In other embodiments, viruses provided herein can be used to treat cancer patients. A particular virus can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). A virus can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., Vero cells or Vero/hSLAM cells) in culture. After 2 to 3 hours of viral adsorption, the inoculum is removed, and cells are overlaid with a mixture of cell culture medium and agarose or methylcellulose (e.g., 2 mL DMEM containing 5% FCS and 1% SeaPlaque agarose). After about 3 to about 5 days, cultures are fixed with 1 mL of 10% trifluoroacetic acid for about 1 hour, then UV cross-linked for 30 minutes. After removal of the agarose overlay, cell monolayers are stained with crystal violet and plaques are counted to determine viral titer.

Viral stocks can be produced by infection of cell monolayers (e.g., adsorption for about 1.5 hours at 37° C.), after adsorption, the inoculum can be removed, and cells overlaid with a mixture of cell culture medium and agarose or methylcellulose (e.g., 2 mL DMEM containing 5% FCS and 1% SeaPlaque agarose). After about 3 to about 5 days, virus isolated from a plaque can be used to infect a new cell monolayer (e.g., adsorption for about 1.5 hours at 37° C.). After about 3 to about 5 days, virus can be harvested by scraping of infected cells into a suitable medium (e.g., Opti-MEM; Gibco/Invitrogen, Carlsbad, Calif.) and freeze/thaw lysis. The cleared supernatants represent "plaque purified" virus. Viral stocks can be aliquoted and frozen, and can be stored at −70° C. to −80° C. at concentrations higher than the therapeutically effective dose. A viral stock can be stored in a stabilizing solution. Stabilizing solutions are known in the art and include, without limitation, sugars (e.g., trehalose, dextrose, or glucose), amino acids, glycerol, gelatin, monosodium glutamate, $Ca^{2+}$, and $Mg^{2+}$.

Methods described herein are useful for treating cancer (i.e., reducing tumor size, inhibiting tumor growth, or reducing the number of viable tumor cells). As used herein, "reducing the number of viable tumor cells" is meant to encompass (1) slowing the rate of growth of a population of tumor cells such that after a certain period of time, a tumor in a treated individual is smaller than it would have been without treatment; (2) inhibiting the growth of a population of tumor cells completely, such that a tumor stops growing altogether after treatment; and/or (3) reducing the population of tumor cells such that a tumor becomes smaller or even disappears after treatment.

Viruses provided herein can be administered to a cancer patient by, for example, direct injection into a group of cancer cells (e.g., a tumor) or intravenous delivery to cancer cells. Types of cancer cells susceptible to treatment with viruses include neuronal cells, glial cells, myelomonocytic cells, and the like. Methods described herein can be used to treat types of cancer that include, but are not limited to, myeloma, melanoma, glioma, lymphoma, and cancers of the lung, brain, stomach, colon, rectum, kidney, prostate, ovary, and breast. An attenuated measles virus containing a modified H polypeptide can be used to treat, for example, a lymphoma (e.g., Non-Hodgkin's Lymphoma).

Viruses containing polypeptides that have H polypeptide amino acid sequences coupled to a second amino acid sequence can be particularly useful for treating cancer or reducing tumor growth. For example, a virus containing an H polypeptide coupled to a growth factor amino acid sequence can target cells (e.g., tumor cells) that have growth factor receptors on their surface.

Viruses provided herein can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe as a vaccine (e.g., $10^3$ pfu) and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

Viruses provided herein can be delivered in a dose ranging from, for example, about $10^3$ pfu to about $10^{12}$ pfu (typically $>10^8$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same or a different modified virus) can be administered by the same route as initially used or by another route. A therapeutically effective dose can be delivered in several discrete doses (e.g., days or weeks apart) and in one embodiment, one to about twelve doses are provided. Alternatively, a therapeutically effective dose of attenuated measles virus can be delivered by a sustained release formulation.

Viruses provided herein can be administered using a device for providing sustained release. A formulation for sustained release of a virus can include, for example, a polymeric excipient (e.g., a swellable or non-swellable gel, or collagen). A therapeutically effective dose of a virus can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. Alternatively, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

Viruses provided herein can be directly administered. For example, a virus can be injected directly into a tumor (e.g., a lymphoma) that is palpable through the skin. Ultrasound guidance also can be used in such a method. Alternatively, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of a virus also can be directly administered to a group of cancer cells that is visible in an exposed surgical field.

Viruses provided herein also can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of virus therapy can be monitored by evaluating changes in clinical symptoms (known in the art for each particular type of cancer) or by direct monitoring of the size of a group of cancer cells or tumor. A method for using a virus to treat cancer is considered effective if the cancer cell number, tumor size, tumor specific antigen level, and/or other clinical symptoms are reduced by at least 10 percent following administration of virus. For a solid tumor, for example, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

The invention will be further described in the following examples, which do not limit the scope of the invention described in the claims.

EXAMPLES

Example 1

Materials and Methods

Cells:

The human lung cell lines H358 (ATCC CRL-5807), H441 (ATCC HTB-174), H23 (ATCC CRL-5800), and H522 (ATCC CRL-5810) were maintained in RPMI 1640 medium supplemented with 2 mM L-glutamine and adjusted to contain 1.5 g/L sodium bicarbonate, 4.5 g/L glucose, 10 mM HEPES, 1 mM sodium pyruvate, and 10% FCS. The human bladder cell line, SCaBER (ATCC HTB-3) was maintained in minimum essential medium (MEM) supplemented with 2 mM L-glutamine and Earle's balanced salt solution (BSS) adjusted to contain 1.5 g/L sodium bicarbonate, 0.1 mM non-essential amino acids, 1 mM sodium pyruvate, and 10% fetal calf serum (FCS). The bladder cell line T24 (ATCC HTB-4) was maintained in McCoy's 5a medium supplemented with 1.5 mM L-glutamine, 2.2 g/L sodium bicarbonate, and 10% FCS. The bladder cell line HT-1376 (ATCC CRL-1472) was maintained in MEM in Earle's BSS with non-essential amino acids, and 10% FCS. Vero cells (African green monkey kidney, ATCC CCL-81), and B95a, a marmoset B-cell line (provided by D. Gerlier), were maintained in Dulbecco's modified Eagle's medium (DMEM) supplemented with 10% FCS. The rescue helper cell line 293-3-46 (Radecke et al., 1995, *Embo J.* 14:5773-5784) was grown in DMEM with 10% FCS and 1.2 mg of G418/mL. Vero/hSLAM cells (provided by Y. Yanagi) were maintained in DMEM supplemented with 10% FCS and 0.5 mg of G418/mL.

Viruses:

Wild-type MV strains wtD4 and wtD8 (provided by P. Rota, Centers for Disease Control and Prevention, Atlanta, Ga.) (Riddell et al., 2005, *Virol. J.* 2:87) were isolated and propagated on Vero/hSLAM cells for three passages prior to use. MV strain wtH1 (provided by P. Rota) was isolated on B95a cells prior to propagation on Vero/hSLAM cells. Recombinant viruses were recovered using the plasmid p(+)MV323 (Takeda et al., 2000, *J. Virol.* 74:6643-6647), coding for WT genome.

Recombinant MVs were generated as described by Radecke et al., supra, but rescue cells were overlaid with cells expressing an appropriate receptor. Depending on the mutation, the viruses were propagated on Vero/hSLAM or H358 cells. To prepare virus stocks, Vero/hSLAM or H358 cells were infected at an MOI of 0.03 with the relevant virus and incubated at 37° C. Cells were scraped in Opti-MEM (Invitrogen, Carlsbad, Calif.), and particles released by one freeze-thaw cycle. Titers were determined by 50% end-point titration on Vero/hSLAM or H358 cells according to the Spearman-Kärber method. See Kärber, 1931, *Arch. Exp. Pathol. Pharmakol.* 162:480-483.

Plasmids and Mutagenesis:

The expression plasmid, pCG-IC323-H, was obtained by digesting the plasmid p(+)MV323, coding for WT genome, with PacI/SpeI enzymes (FIG. 1A). The DNA fragment encoding the H gene was subcloned into the PacI/SpeI digested pCG plasmid (Huber et al. (1991) *Virology* 185: 299-308). The plasmid pCG-IC323-F was produced by PCR amplification of the F ORF using the forward primer CCT-TAATTAAATGGGTCTCAAGGTGAACGT (GenBank NC_001498, underlined nucleotide at position 5458, SEQ ID NO:7), and reverse primer AGCTTTGTTTAAAC TCAGAGCGACCTTACATAGGATT (underlined nucleotide at position 7110, SEQ ID NO:8), digesting the PCR product with PacI/PmeI enzymes and subcloning the fragment into PacI/PmeI-digested pCG plasmid.

Mutations in the wild type H open reading frame were introduced by QuikChange site directed mutagenesis (Stratagene, La Jolla, Calif.) using pCG-IC323-H as a template. For construction of the eGFP expressing $WT_{green}$, an additional transcription unit (Duprex et al., 1999, *J. Virol.* 73:9568-9575) was inserted in the EcoRV restriction site located at base 100 of WT genome, upstream of the N gene. This additional transcription unit is composed of the complete eGFP open reading frame followed by the viral transcription stop sequence, the intergenic region, and the viral transcription start sequence of the N/P genes. Selected H mutants were transferred into $WT_{green}$ genome by moving the mutated PacI/SpeI fragment from pCG-IC323-H into PacI/SpeI digested p(+)MV323 containing the additional transcription unit. All engineered MV genomes were of hexameric length.

Virus Growth Kinetics:

Virus growth kinetics were performed at an MOI of 0.03 for 1 hour at 37° C. Infected cells were washed 3 times with Opti-MEM and returned to 37° C. At the indicated times, supernatants were clarified by centrifugation, cells scraped in Opti-MEM and subjected to one freeze-thaw cycle. Released and cell-associated viral titers were determined by TCID50 titration.

Fusion Assays:

Cells seeded on 6-well tissue culture plates were allowed to reach 80% confluence prior to transfection. Equal amounts (2 μg) of pCG-IC323-F, the mutated pCG-IC323-H, and eGFP-expressing pEGFP-N1 (Clontech, Mountain View, Calif.) were transfected using Lipofectamine 2000 (Invitrogen, Carlsbad, Calif.) according to the manufacturer's protocol. The extent of fusion was assessed by determining the area of syncytia formation in a representative field of view 24 h post transfection. The fields of view area was 1200 μm×900 μm and contained typically 2,000 Vero/hSLAM cells or 1,300 H358 cells at the time of assessment. In Vero/hSLAM cells a syncytium was defined as a cell with five or more nuclei. The levels of fusion in Vero/hSLAM were reported with the following notation: white rectangles, two or less syncytia per field of view; one-third filled rectangle, less than 50% of the nuclei located in syncytia; two-thirds filled rectangle, between 50% and 90% of the nuclei located in syncytia; completely filled rectangle, over 90% of the nuclei located in syncytia. Since fusion was less extensive in H358 than in Vero/hSLAM cells, different thresholds were used, and only two levels of fusion above background were considered: white rectangles, no syncytia found; half filled rectangle, less than 8% of the nuclei located in syncytia; completely filled rectangle, 9-12% of the nuclei located in syncytia. A fusion score was assigned for each mutant after at least three independent experiments.

Homology Modeling of the H Protein:

The procedure used to create the model of the MV Edmonston B vaccine lineage H protein based on the structure of the Newcastle disease virus HN protein (Crennell et al., 2000, *Nat. Struct. Biol.* 7:1068-1074) was published by Vongpunsawad et al., 2004, *J. Virol.* 787:302-313. The MV Edmonston B vaccine lineage H protein differs from the wild type H protein by only 10 amino acids scattered over the whole sequence. The local side chain orientations close to these substitutions were expected to adjust without changing the overall global fold. The MV H-Newcastle disease virus HN protein alignment was used. The sequence of the Edmonston B was replaced with the wild type H protein, and a structural model was generated. The model was further refined by energy minimization with FANTOM (Thomas et al., 1990, *Biopolymers* 29:679-694). The 3D representations of the structure were produced with MOLMOL software.

Infection of Rhesus Monkeys:

Colony-bred male and female juvenile rhesus monkeys (*Macaca mulatta*), seronegative for MV, were housed in accordance with guidelines of the American Association for Accreditation of Laboratory Animal Care. For consistence with previous experiments, the $TCID_{50}$ of the virus stock was determined by endpoint dilution co-culture with Raji cells. Six animals were inoculated with $10^{4.5}$ $TCID_{50}$ of $WT\text{-}H_{DOUBLE}$ in a volume of 1 mL by a single drop into the conjunctiva of each eye and the remainder divided into both nares. The animals were monitored daily for clinical symptoms including anorexia, depression, coughing, diarrhea, and skin rash. They were bled under Ketamine sedation on days 0, 7, 14 21, and 28 post-infection and viremia was quantified by end point dilution co-culture with Raji cells. At the same time point tracheal aspirates and urine samples were taken, centrifuged and the cell pellet tested for MV by co-culture with Raji cells. Neutralizing antibody to MV was measured as described by Zhu et al. (1997) *Virology* 233: 85-92.

Infection of Polarized Human Airway Epithelial Cells:

Primary cultures of human airway epithelia were prepared from trachea and bronchi by enzymatic dispersion and seeded onto collagen-coated, semi-permeable membranes with a 0.4 μm pore size (Millicell-HA; surface area 0.6 $cm^2$; Millipore Corp, Billerica, Mass.) (Zabner et al., 1996, *J. Virol.* 70:6994-7003). Only well-differentiated cultures (>2 weeks old; resistance >500 $cm^2$) were used in these studies. MV preparations were diluted in sterile 1× phosphate buffer saline (PBS) to an MOI of 0.1 and 100 μL of the solution was applied to the apical or basolateral surface of airway epithelial cells (0.1 MOI) as described by Sinn et al., 2002, *J. Virol.* 76:2403-2409. After incubation for 4 hours at 37° C., the inoculum was removed, and cells were washed and further incubated at 37° C. for the indicated time periods. A Xenogen IVIS CCD camera was used for biofluorescent imaging of infected cultures, and fluorescence intensity quantified using Xenogen Living Image software.

To determine the polarity of viral release from basolaterally infected airway epithelia, 500 μL washings were collected both from the apical and basolateral surfaces of airway epithelia at progressing time points and used to infect Vero/hSLAM cells. Virus-inoculated plates were centrifuged at 200 g at room temperature for 10 min. Titers were calculated by counting eGFP positive cells after 30 hours.

Transepithelial resistances were measured using a volt-ohm meter (World Precision Instruments, Sarasota, Fla.). Values were corrected for the blank filter resistance and further standardized against baseline readings and uninfected counterparts. Neither corrected nor raw numbers resulted in a statistically significant variation from uninfected epithelia.

Example 2

MV Infects Human Epithelial Cells Independently of SLAM

To facilitate analysis of the permissivity of human epithelial cell lines to wild type MV infection, the wild type molecular clone MVwtIC323 (herein named WT) was engineered to express the enhanced green fluorescent protein (eGFP) from an additional transcription unit (FIG. 1A). $WT_{green}$ reached equivalent titers, with similar kinetics, as MVwtIC323 (data not shown).

To identify permissive epithelial cells, seven transformed cell lines of different origins were chosen: H358 and H441 are bronchio-alveolar carcinoma and papillary adenocarcinoma cells, respectively, whereas H23 and H522 cells derive from adenocarcinoma. In addition, three carcinoma cell lines from the human bladder transitional epithelium were selected, SCaBER, T24, and HT-1376.

$WT_{green}$ infected H358 and H441 lung cells, and HT-1376 bladder cells but not the other epithelial cell lines tested (FIG. 1B). As expected, this wild type virus infected control cell lines expressing SLAM (B95a and Vero/hSLAM cells), but not a control cell line expressing only CD46 (Vero). SLAM, the only known receptor for wild type MV, was not detected by flow cytometry analysis on the surface of HT-1376, H441 and H358 cells (data not shown). Vaccine lineage $MVvacNS_{egreen}$ (Duprex et al. (1999) *J. Virol.* 73:9568-9575) infected every cell type through the ubiquitous protein CD46. Thus three cell lines were identified from MV target organs expressing an unidentified receptor, EpR, allowing wild type MV entry.

Figure 1C:
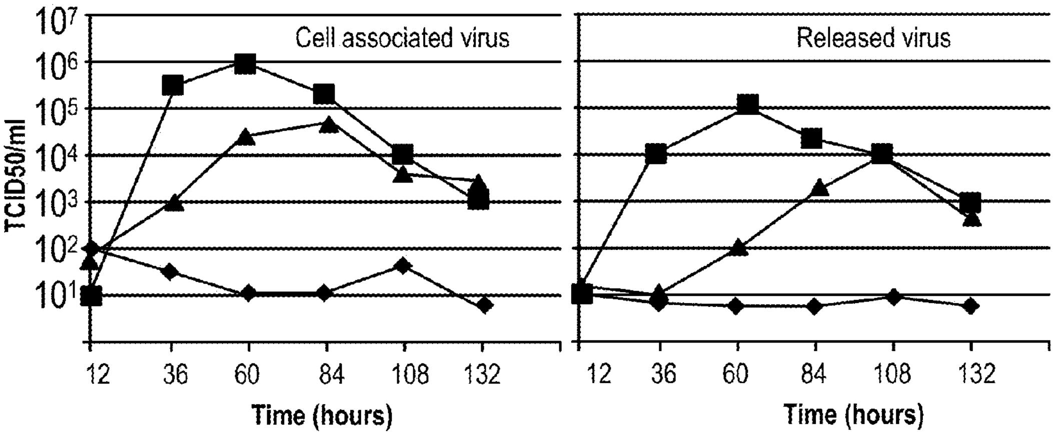
FIG. 1C contains two graphs of viral growth kinetics of cell associated (right panel) or released (left panel) $WT_{green}$ following H358 (triangles), Vero/hSLAM (squares), or Vero (diamonds) cells infection. Viral titers are indicated as $TCID_{50}$/mL.

To compare growth of the wild type virus on EpR- and SLAM-expressing cells, the infection of H358, Vero/hSLAM and Vero cells by $WT_{green}$ was monitored over 6 days (FIG. 1C). In H358 cells (triangles), the virus replicated efficiently, reaching titers of $10^5$ 50% tissue culture infectious dose ($TCID_{50}$) per mL for cell-associated virus, and $10^4$ $TCID_{50}$/mL for released virus. These titers are about 10 times lower than in Vero/hSLAM cells (squares). The peak of viral production was delayed in H358 cells compared to Vero/hSLAM, consistent with the slower doubling time of H358 cells (38 hours) as opposed to Vero/hSLAM cells (20 hours). As expected, viral production in Vero cells (diamonds) was at background levels.

Figure 1D:
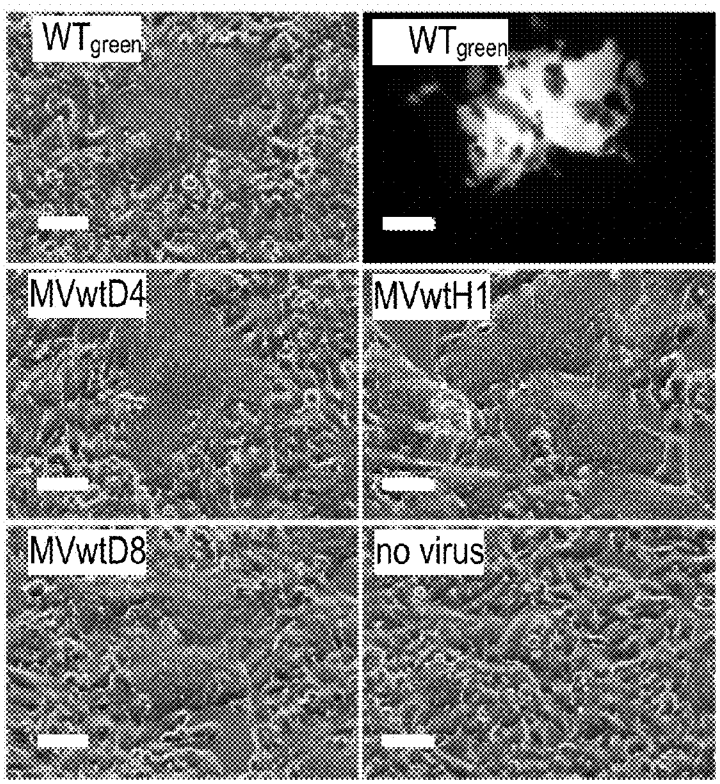
FIG. 1D contains a series of photomicrographs indicating the permissivity of H358 cells to infection with MV wild type strains. $WT_{green}$ infection analysis is shown on the top row in phase contrast (left panel) or fluorescence emission (right panel). Infections with MVwtD4, MVwtH1 and MVwtD8 are shown in the middle and bottom rows. Pictures were taken 48 hours post-infection. Scale bars: 100 μm.

To assess whether other wild type strains infect H358 cells, three clinical isolates (MVwtD4, MVwtD8, and MVwtH1) known to enter cells via SLAM but not CD46 (Condack et al., 2007, *J. Infect. Dis.* 196:541-549) were used. These viruses produced syncytia within 48 hours (FIG. 1D). Taken together, these data confirm the presence of an unidentified receptor, EpR, for wild type MV on the surface of certain human lung and bladder human epithelial cells, sustaining virion-to-cell and cell-to-cell fusion.

Example 3

Residues in Hemagglutinin Beta-Sheets 4 and 5 Sustain EpR-Dependent Fusion

Figure 2A:
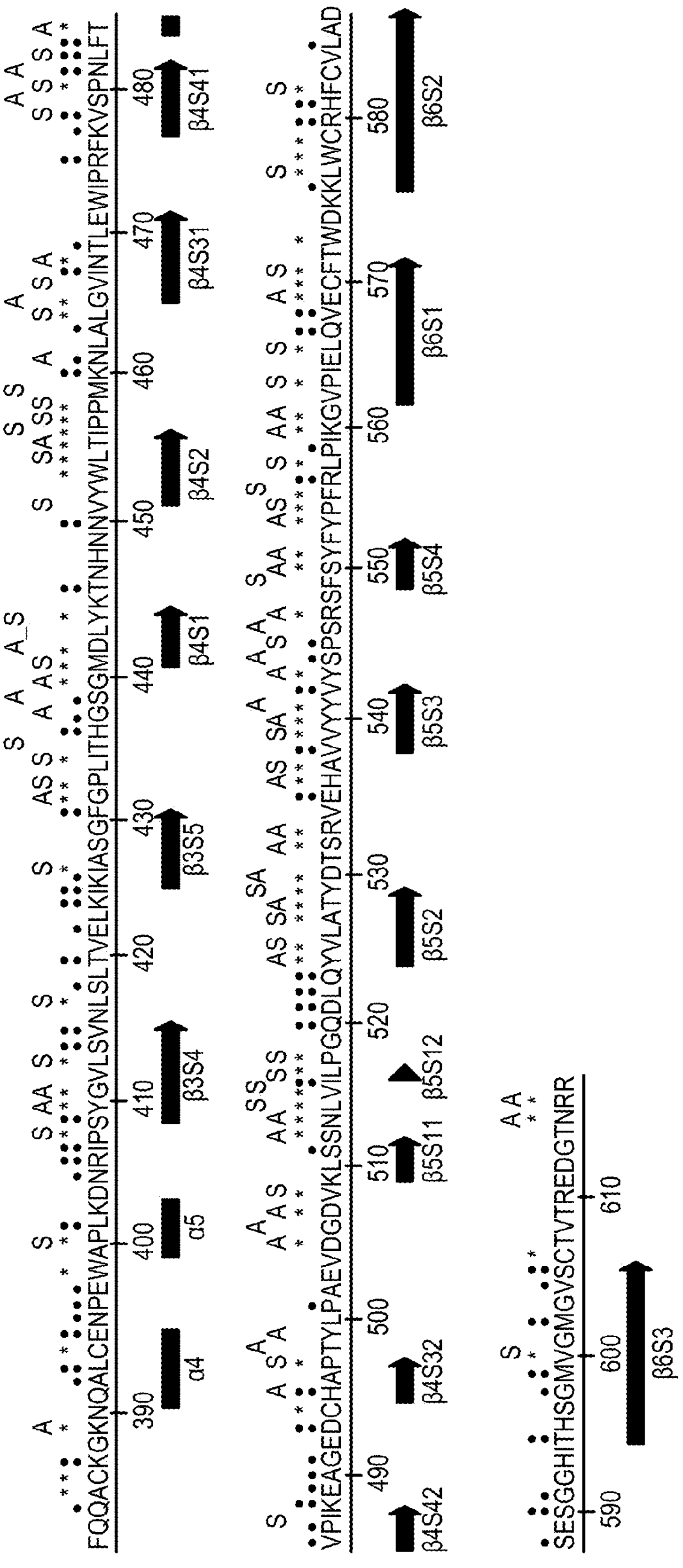
FIG. 2A is a listing of the amino acid sequence of residues 382-617 of the wild type MV H protein (SEQ ID NO:6). Identity or homology of MV H to the corresponding sequences of CDV and RV H proteins (accession number NP_056923, AAD18008 and AAD25093, respectively) are indicated as follows: (*) identical residues, (:) conserved residues, (.) semi-conserved residues. The letters above the alignment denote the mutants produced as single (individual letter) or double substitutions (contiguous residues; only the double mutant 442-444 is not contiguous). Alanine (A) or serine (S) were used to replace polar and apolar residues, respectively. The H protein secondary structure is shown below the MV H sequence, with arrowed lines indicating beta-sheets and boxes indicating alpha-helixes.
Figure 2B:
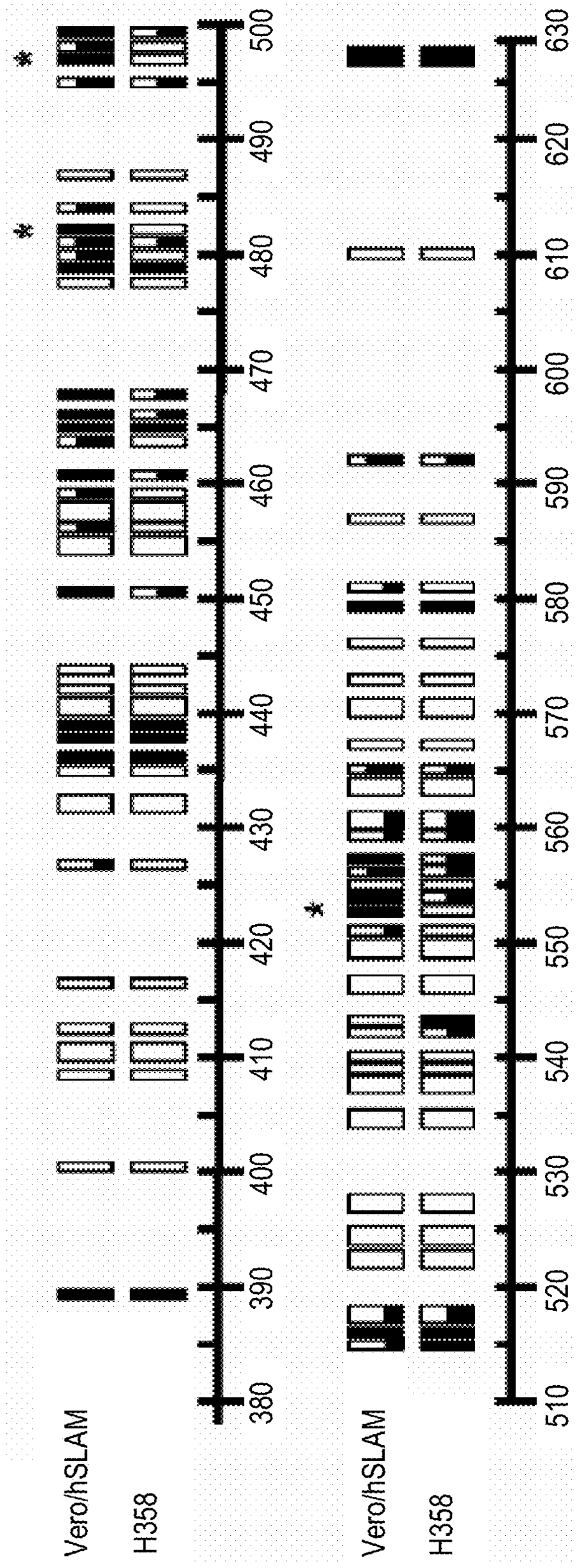
FIG. 2B is a schematic of the fusion efficiency of the H-protein mutants in Vero/hSLAM or H358 cells. Each mutant is represented as a rectangle located at the appropriate position in the sequence. Filled (black) rectangles indicate full fusion activity; white rectangles indicate no fusion activity; partially filled rectangles indicate intermediate fusion levels as described in Methods. Mutants with unaltered SLAM-mediated fusion and no EpR-mediated fusion are highlighted with asterisks.

To identify H protein residues important for EpR-dependent fusion support, an iterative mutagenesis protocol and assays measuring EpR— or SLAM-dependent fusion were used. Based on analyses of the H protein residues or epitopes available for interaction (Hu et al., 1993, *Virology* 192:351-354; Santiago et al., 2002, *J. Biol. Chem.* 277:32294-32301; Sheshberadaran et al., 1986, *Virology* 152:58-65; Vongpunsawad et al., 2004, supra), mutagenesis was focused on amino acids 382 to 617 (SEQ ID NO:6; full length sequence set forth in SEQ ID NO:1). It was hypothesized that the EpR interaction is conserved within viruses of the Morbillivirus genus, as is the case for SLAM binding, and therefore all the H protein amino acids conserved between the three morbilliviruses MV, rinderpest virus (RV), and canine distemper virus (CDV) were mutated (FIG. 2A). Alanine and serine were used to substitute polar and apolar residues, respectively. Conserved cysteine and tryptophan residues were not mutated to preserve the protein structure and hydrophobic core. The fusogenic activity of 48 mutant proteins was scored in two fusion assays based on complementation with the F protein, one performed in EpR-expressing H358 and the other in SLAM-expressing Vero/hSLAM cells (FIG. 2B). Levels of fusion were defined as described in Example 1.

Four residues with EpR-selective fusion support function (I456, L464, P497, and Y543) were identified during the first round of mutagenesis and receptor-dependent functional screening. These residues were located on a model of the WT H protein ectodomain (residues 145 to 617) developed as previously described for a vaccine strain H protein. This model, which predicted correctly the global folding of the MV H protein, was used to plan a second round of mutagenesis. All of the amino acids predicted to be located within 10 Å of I456, L464, P497 or Y543, and solvent-exposed, were mutated. The results of these two rounds of mutagenesis are shown on the recently published H protein crystal structure. This structure is visualized in FIG. 2C in a ribbon plot representation (left-panel), and in a space filling representation (right panel). Both panels show the H protein from the top, illustrating a superbarrel in which 6 beta-sheets are arranged cyclically around an axis.

Of the 69 mutants analyzed during both mutation rounds, 9 maintained full fusion support in both cell lines (FIG. 2B, black rectangles), and 30 lost completely fusion capacity in both cell lines (FIG. 2B, white rectangles). Twelve mutants had no fusion support capacity in H358 epithelial cells but maintained at least partial fusion support in Vero/hSLAM cells (FIG. 2B). Three of these mutants maintained low fusion support in Vero/hSLAM (I427S, Y541A, F571S), 6 retained most fusion support (I456S, M459S, L464S, P480S, T484A, T498A), and 3 completely retained SLAM-dependent fusion support (L482S, P497S, Y543A, asterisks in FIG. 2B).

Figure 2C:
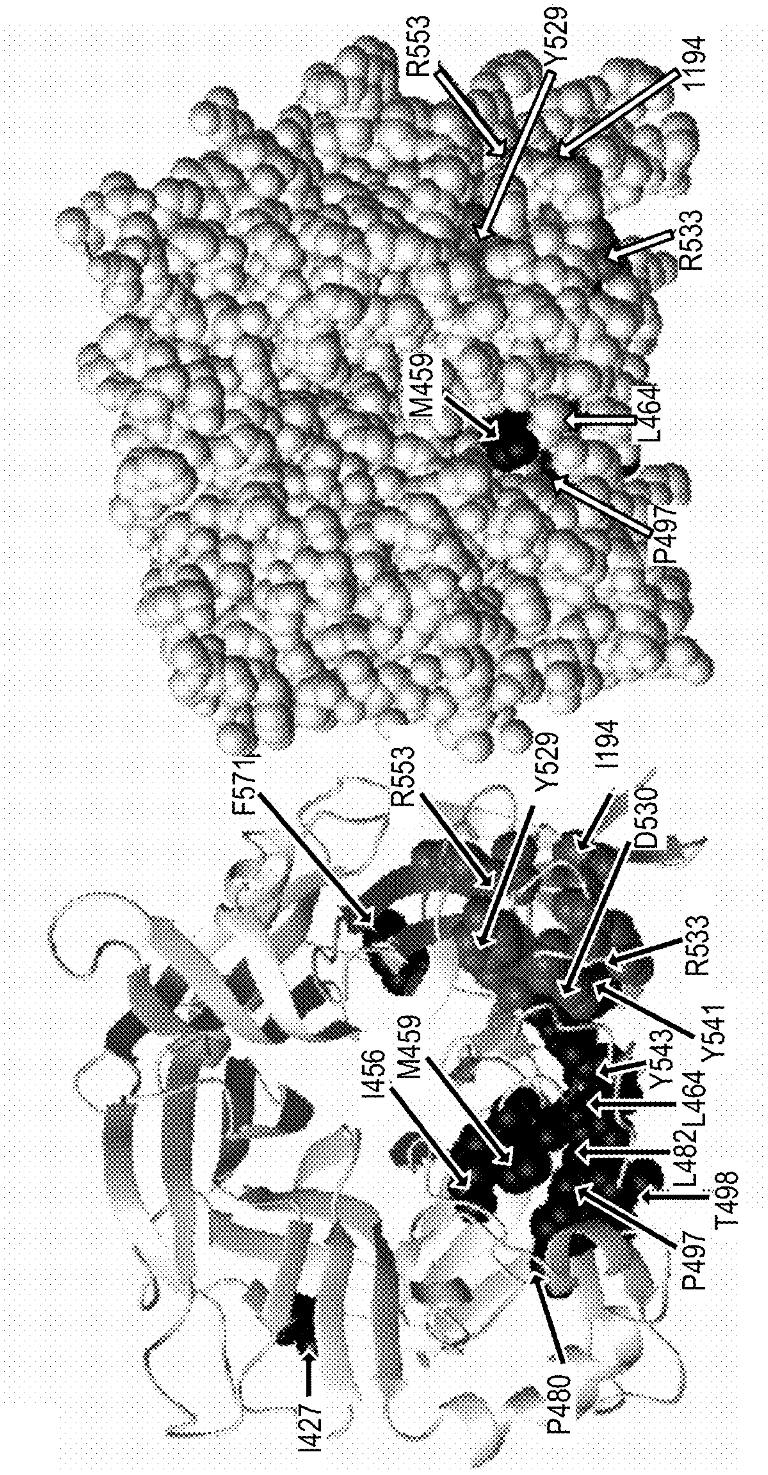
FIG. 2C contains a top view of the H protein crystal structure in a ribbon plot (left panel) and space filling (right panel) representation. The residues whose mutation abolished EpR-dependent fusion are shown in black. Residues important for SLAM-induced fusion are shown in gray.

These residues are shown in black on the crystal structure (FIG. 2C). Eight out of the nine residues whose mutations partially impaired SLAM-dependent fusion are clustered in one region of the protein, centered around the three residues L482S, P497S, Y543A and located in beta-sheets 4 and 5 (FIG. 2C, left panel; see also space-filling representation in right panel). One residue essential for SLAM binding (I194) (Navaratnarajah et al. (2008) *J. Biol. Chem*. Doi:10.1074/jbc.M800896200) and four essential for SLAM-dependent fusion Y529, D530, R533, and Y553 are shown in grey in both panels of FIG. 2C. Thus, residues relevant for EpR-dependent fusion are located in beta-sheets 4 and 5 of the H protein, while those relevant for SLAM-dependent fusion are located on beta-sheet 5.

Example 4

Generation of Selectively EpR-Blind MV

To determine the role of the EpR in virulence, selectively EpR-blind MV were generated. Among the H protein mutants characterized above, those retaining 100% fusion activity in Vero/hSLAM and without fusion activity in H358 cells (L482S, P497S, and Y543A) were selected. These residues have an uncharged polar (Y543) or non-polar (L482 and P497) side chains. After confirming expression and stability of the corresponding proteins in both cell lines, the mutations were transferred into the backbone to generate $WT_{green}$-$H_{482}$, $WT_{green}$-$H_{497}$, $WT_{green}$-$H_{543}$, and the double $WT_{green}$ mutant with the mutations P497S/Y543A, $WT_{green}$-$H_{DOUBLE}$.

As a control, a selectively SLAM-blind wild type MV was generated. Towards this, the functionality of the four mutations in the H protein of the vaccine strain known to abrogate SLAM-dependent fusion (Y529A, D530A, R533A, and Y553A) was tested in H358 cells after re-cloning in the wild type H protein background. The mutations Y529A, D530A, and Y553A abrogated SLAM-dependent fusion but also partially inhibited EpR-dependent fusion. The mutation R533A fully preserved fusion capacity in H358 cells and was therefore selected to generate $WT_{green}$-$H_{SLAMblind}$.

Figure 3:
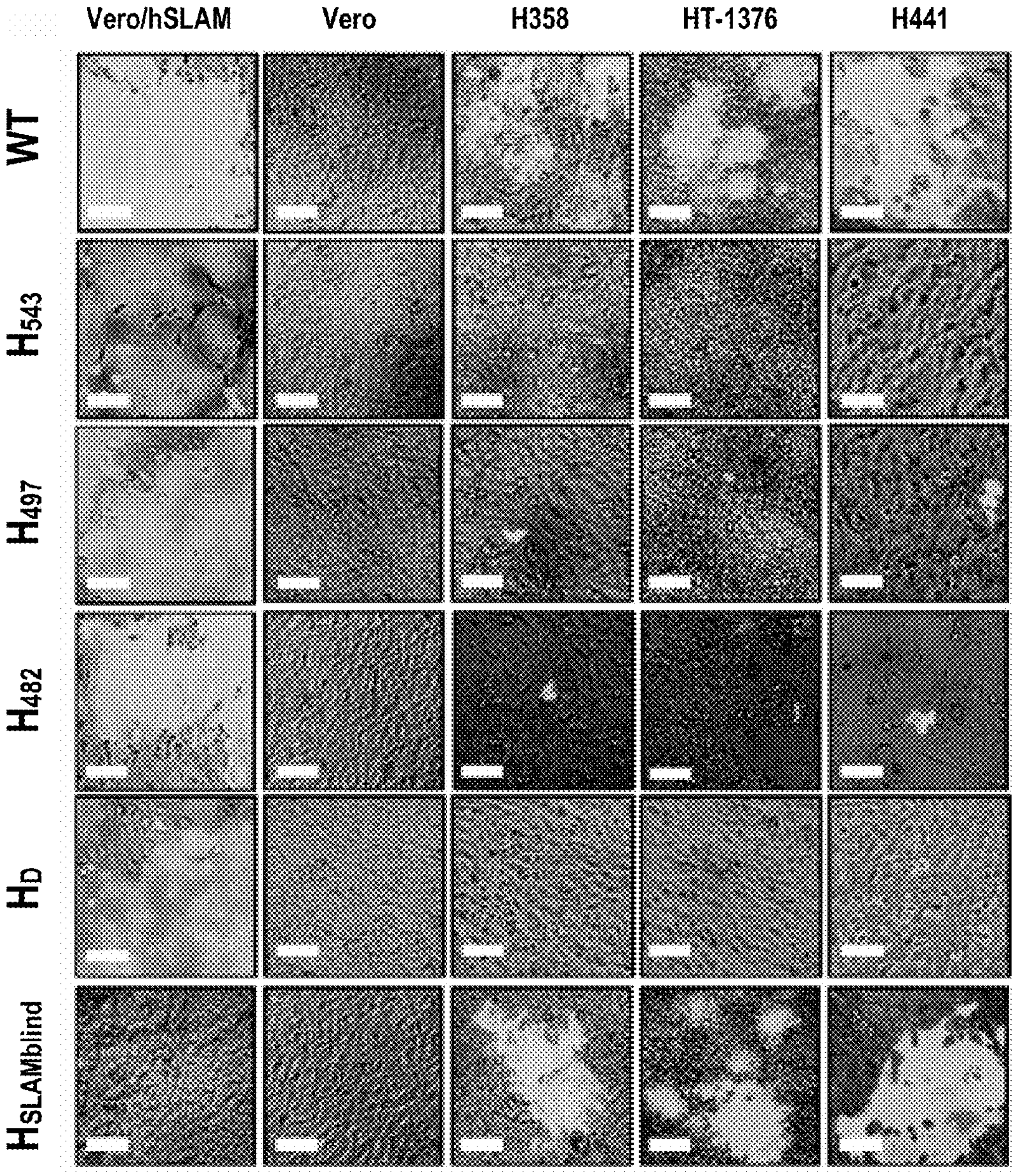
FIG. 3 is a series of phase contrast pictures of cells that were overlaid with fluorescence microscopy images. $WT_{green}$ (WT) and the mutant viruses $WT_{green}$-$H_{543}$ (H543), $WT_{green}$-$H_{497}$ ($H_{497}$), $WT_{green}$-$H_{482}$ ($H_{482}$), $WT_{green}$-$H_{DOUBLE}$ ($H_D$), and $WT_{green}$-$H_{SLAMblind}$ ($H_{SLAMblind}$) were used to infect Vero/hSLAM cells, Vero cells, or the three epithelial cell lines H358, HT-1376, and H441. The scale bars represent 100 μm.

The receptor specificity of the recombinant MV was analyzed on SLAM- or EpR— expressing cell lines (FIG. 3). $WT_{green}$-$H_{543}$ completely lost competence to infect the three human epithelial cell lines H358, HT-1376, and H441. $WT_{green}$-$H_{497}$ and $WT_{green}$-$H_{482}$ infected these epithelial cells, but with much lower efficiency and greatly reduced fusion capacity compared to $WT_{green}$. On the other hand, all three viruses efficiently infected Vero/hSLAM cells. These results show that $WT_{green}$-$H_{543}$ is EpR-blind, and $WT_{green}$-$H_{482}$ and $WT_{green}$-$H_{497}$ are EpR-impaired. The double mutant $WT_{green}$-$H_{DOUBLE}$ did not infect any of the epithelial cell lines, but it had somewhat reduced fusion efficiency in Vero/hSLAM cells. $WT_{green}$-$H_{SLAMblind}$ was unable to infect Vero/hSLAM cells, but efficiently infected the three epithelial cell lines. None of the recombinant viruses infected Vero cells, confirming a lack of interaction with CD46. Thus selectively EpR- and selectively SLAM-blind mutant MVs were generated.

Example 5

Selectively EpR-Blind MV Remains Virulent in Macaques

To assess the role of the EpR, rhesus monkeys (*Macaca mulatta*), a primate species developing a measles-like illness, were infected. Six animals were inoculated intranasally with WT-$H_{DOUBLE}$ to minimize the probability of selecting revertants during viral replication in the animal. A virus that does not express GFP was used to avoid the possibility of loss of virulence (von Messling et al., 2004, *Proc. Natl. Acad. Sci. USA* 101:14216-14221). Viremia was measured 7 and 14 days post-inoculation. WT-$H_{DOUBLE}$ was detected in the PBMC of all 6 hosts at day 7 post-inoculation, the peak of viremia in monkeys infected with WT, at titers about 10 times lower than WT (FIG. 4A). Similarly, titers 5-10 times lower than for the WT were detected 14 days after inoculation, with 4 animals having cleared infection.

Development of clinical signs was followed over 28 days (FIG. 4B). The EpR-blind infected macaques developed measles signs comparable to those of the animals infected with the wild type virus, including rash and anorexia. The humoral immune response, as measured by levels of neutralizing antibodies, was similar in titer and kinetics in animals inoculated with WT-$H_{DOUBLE}$ or WT (FIG. 4C). Thus, systemic infection and some clinical signs of measles are independent of epithelial cell infection.

Example 6

A Selectively EpR-Blind MV is not Shed

This experiment was performed to determine whether infectious virus was secreted into body fluids from the respiratory and urinary epithelia. Wild type MV is commonly detected in urine samples and throat swabs of infected patients and mucosal shedding has been documented in vaccinated infants (Rota et al. (1995) *J. Clin. Microbiol.* 33:2485-2488). Moreover, the wild-type MV strain IC-B used in this study was secreted in nasal aspirates of infected rhesus monkeys from day 4 to 14 post-inoculation (de Swart et al., 2007, supra). Tracheal aspirates and urine samples were collected from monkeys infected with WT-$H_{DOUBLE}$ at 0, 7, 14, 21, or 28 days following inoculation. WT-$H_{DOUBLE}$ was not isolated from any of these samples (FIG. 4B). These results indicate that the EpR-blind virus is not shed.

Example 7

Wild Type MV Uses EpR to Enter Human Airway Epithelium Basolaterally

To characterize the polarity of MV entry into respiratory epithelium, primary cultures of well-differentiated human airway epithelial cells were used. This reconstituted epithelial sheet, cultured at an air-liquid interface, closely resembles the human airway. The primary cells develop tight junctions and a well-differentiated morphology consisting of a pseudostratified, ciliated columnar epithelium with goblet and basal cells (Karp et al., 2002, *Methods Mol. Biol.* 188:115-137). Using this epithelial sheet culture, it has been shown that $MVvacNSe_{green}$, a CD46-binding vaccine strain, preferentially infects epithelial cells from the basolateral side (Sinn et al. (2002) *J. Virol.* 76:2403-2409).

Figure 5A:
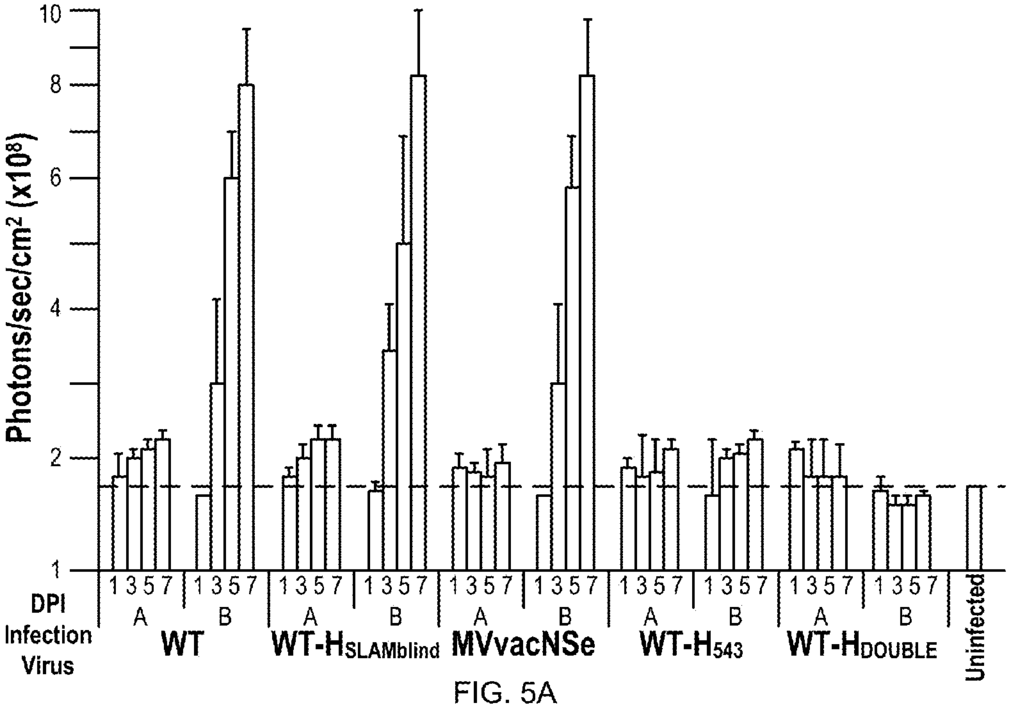
FIG. 5A is a graph of MV infection quantified by biofluorescent imaging following apical (A) or basolateral (B) infection. Measurements were performed at days 1, 3, 5, and 7 post-infection (DPI) as indicated. Fluorescence intensity of eGFP is expressed as the radiance units of photons per second that are leaving a square centimeter of tissue and radiating into a solid angle of one steradian (photons/sec/$cm^2$/sr). The dashed line indicates the average values of the uninfected sample.

$WT_{green}$, $WT_{green}$-$H_{SLAMblind}$, $MVvacNSe_{green}$, and the two EpR-blind viruses $WT_{green}$-$H_{543}$, and $WT_{green}$-$H_{DOUBLE}$ were applied either to the apical or basolateral surface of epithelial sheets. Infection was quantified by measurement of eGFP fluorescence. As shown in FIG. 5A, infection with $WT_{green}$ was efficient only upon virus application to the basolateral surface. $WT_{green}$-$H_{SLAMblind}$, was as efficient as $WT_{green}$ in basolateral infection. In contrast, application of $WT_{green}$-$H_{543}$ and $WT_{green}$-$H_{DOUBLE}$ at either the apical or basolateral cell surface resulted in no detectable infection, demonstrating a specific requirement for EpR.

Figure 5B:
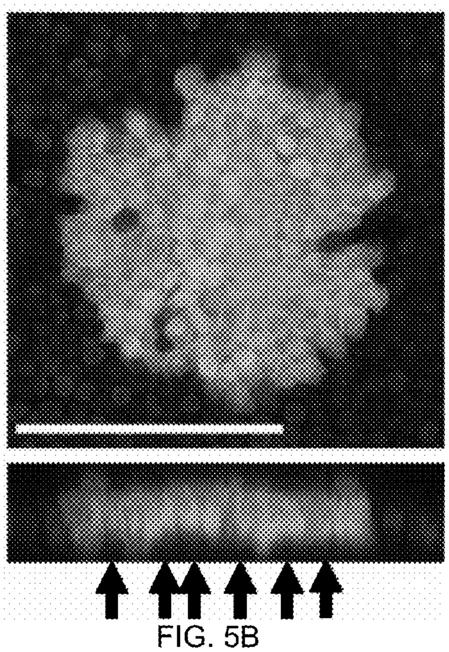
FIG. 5B is a confocal image of basolaterally infected human primary airway epithelial cells. The cells were infected with the indicated viruses at an MOI of 0.1. The bottom panel is a vertical section of the top panel. Scale bar=100 μm. Arrows indicate uninfected basal cells. Confocal images were captured with a Bio-Rad radiance 2100 multiphoton confocal microscope.

Sequential observation of epithelial sheets infected with $WT_{green}$ using confocal microscopy revealed infectious centers that increased in size over time, but cells remained well defined and syncytium formation was not detected (FIG. 5B). Moreover, these observations revealed cell-type selectivity of infection. The epithelia used in these experiments are mainly composed of basal cells located at the base of the epithelium, and ciliated columnar cells spanning the epithelium and providing the tight junctions. Remarkably, analysis of vertical sections of several infectious centers consistently showed that in regions where all columnar cells were infected, no basal cells were infected (FIG. 5B, arrows). Thus wild type MV infects basolaterally polarized columnar cells reaching the luminal surface.

Example 8

Wild Type MV is Shed Apically

Figure 6A:
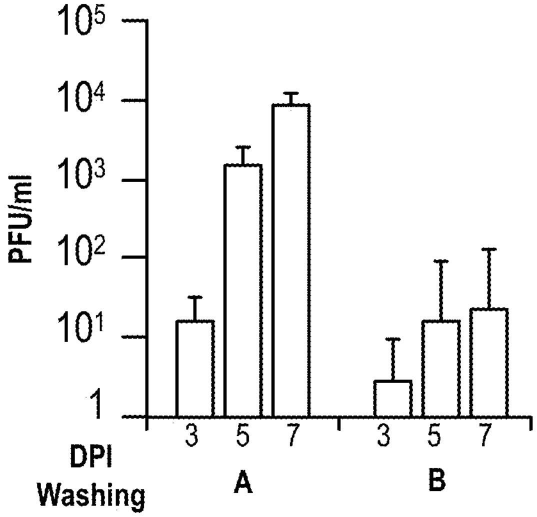
FIG. 6A is a bar graph of the polarity of viral release following MV basolateral infection. Human airway epithelia were infected basolaterally and both apical (A) and basolateral (B) washings were collected over the time intervals indicated. Washing titers were determined on Vero/hSLAM cells. Error bars represent the standard deviation. n=3.
Figure 6B:
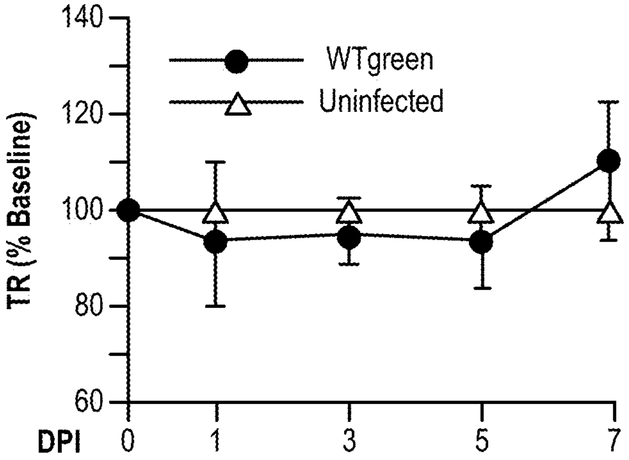
FIG. 6B is a line graph of the maintenance of epithelial integrity following MV infection. Epithelial integrity was determined by ohmmeter measurement of the transepithelial resistance (TR). DPI: days post infection. Error bars represent the standard deviation. n=3.

In order to assay the polarity of viral release, the apical and basolateral surfaces of the $WT_{green}$ infected epithelial sheet were washed at regular time intervals. Viral titers were quantified by measuring plaque forming units on Vero/hSLAM cells. $WT_{green}$ was released almost exclusively at the apical surface of the epithelium (FIG. 6A), reaching ~$10^4$ plaque forming units per mL (pfu/mL) between day 5 and 7 post-inoculation, compared to ~50 pfu/mL released basolaterally. Infection did not compromise transepithelial resistance (FIG. 6B), consistent with lack of syncytia formation or other cytopathic effects. These data demonstrate that following basolateral infection, MV is preferentially shed apically, in what would be the airway lumen in vivo.

In summary, the above examples demonstrate that MV entry into the airway epithelium occurs basolaterally and only in late infection phases, rather than apically immediately after infection. The above examples also indicate that a selectively EpR-blind MV does spread systemically and that host escape-incompetent viruses can be produced.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule, wherein said nucleic acid molecule encodes a polypeptide comprising a hemagglutinin (H) polypeptide amino acid sequence that aligns with and has at least 85 percent identity to the amino acid sequence set forth in SEQ ID NO: 1, wherein said H amino acid sequence comprises an amino acid other than leucine at the position aligning with position 482 of said amino acid sequence, wherein said amino acid other than leucine is serine.

2. The isolated nucleic acid of claim 1, wherein said H polypeptide amino acid sequence further comprises an amino acid other than proline at the position aligning with position 497 of said amino acid sequence or an amino acid other than tyrosine at the position aligning with position 543 of said amino acid sequence.

3. The isolated nucleic acid of claim 2, wherein said H polypeptide amino acid sequence further comprises a serine at the position aligning with position 497 of said amino acid sequence.

4. The isolated nucleic acid of claim 2, wherein said H polypeptide amino acid sequence further comprises an alanine at the position aligning with position 543 of said amino acid sequence.

5. The isolated nucleic acid of claim 2, wherein said H polypeptide amino acid sequence further comprises a serine at the position aligning with position 497 of said amino acid sequence and an alanine at the position aligning with position 543 of said amino acid sequence.

6. The isolated nucleic acid molecule of claim 1, wherein said nucleic acid molecule further encodes an F polypeptide.

7. A cell comprising the isolated nucleic acid molecule of claim 1.

8. The cell of claim 7, wherein said cell is a cell line or a primary cell, wherein said cell line is selected from the group consisting of a Vero cell line, a Vero/hSLAM cell line, and a Jurkat cell line, wherein said primary cell is selected from the group consisting of B lymphocytes, T lymphocytes, dendritic cells, macrophages, and cells from resected primary tumors.

9. A virus comprising the isolated nucleic acid molecule of claim 1.

10. The virus of claim 9, wherein said virus is selected from the group consisting of a measles virus, a canine distemper virus, and a rinderpest virus.

11. The virus of claim 10, wherein said virus is a measles virus.

12. The virus of claim 11, wherein said measles virus is a vaccine strain.

* * * * *

UNITED STATES PATENT AND TRADEMARK OFFICE
CERTIFICATE OF CORRECTION

PATENT NO. : 9,434,768 B2
APPLICATION NO. : 14/249821
DATED : September 6, 2016
INVENTOR(S) : Roberto Cattaneo and Vincent H. J. Leonard It is certified that error appears in the above-identified patent and that said Letters Patent is hereby corrected as shown below:

On the Title Page

Column 1, Line 2 (Assignee), please delete "Rocherster," and insert -- Rochester, --, therefor;

In the Specification

Column 1 (approx. Line 9), Before "371" insert -- § --, therefor.

Signed and Sealed this
Tenth Day of January, 2017

Michelle K. Lee
*Director of the United States Patent and Trademark Office*